United States Patent
Parker et al.

(10) Patent No.: US 12,138,055 B2
(45) Date of Patent: Nov. 12, 2024

(54) IMPLANTABLE ELECTRODE POSITIONING

(71) Applicant: Saluda Medical Pty Ltd, Level (AU)

(72) Inventors: John Louis Parker, Artarmon (AU); Milan Obradovic, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 0 days.

(21) Appl. No.: 18/330,311

(22) Filed: Jun. 6, 2023

(65) Prior Publication Data
US 2023/0309886 A1    Oct. 5, 2023

Related U.S. Application Data

(63) Continuation of application No. 16/752,209, filed on Jan. 24, 2020, now abandoned, which is a (Continued)

(30) Foreign Application Priority Data

Dec. 11, 2014    (AU) ................ 2014905030

(51) Int. Cl.
*A61B 5/24* (2021.01)
*A61B 5/00* (2006.01)
(Continued)

(52) U.S. Cl.
CPC ............... *A61B 5/24* (2021.01); *A61B 5/388* (2021.01); *A61B 5/407* (2013.01); *A61B 5/4893* (2013.01);
(Continued)

(58) Field of Classification Search
CPC ........ A61B 2034/2053; A61B 2505/05; A61B 2562/046; A61B 34/20; A61B 5/1118;
(Continued)

(56) References Cited

U.S. PATENT DOCUMENTS

| | | |
|---|---|---|
| 1,743,835 A | 1/1930 | Stimson |
| 3,724,467 A | 4/1973 | Avery et al. |
| | (Continued) | |

FOREIGN PATENT DOCUMENTS

| | | |
|---|---|---|
| AU | 2013277009 | 1/2016 |
| CN | 101142822 A | 3/2008 |
| | (Continued) | |

OTHER PUBLICATIONS

Balzer et al., "Localization of cervical and cervicomedullary stimulation leads for pain treatment using median nerve somatosensay evoked potential collision testing", Journal of Neurosurgery, Jan. 2011, vol. 114, No. 1 : pp. 200-205.

(Continued)

*Primary Examiner* — Amanda K Hulbert
(74) *Attorney, Agent, or Firm* — Barnes & Thornburg LLP

(57) ABSTRACT

A method of surgically positioning an electrode array at a desired implantation location relative to a nerve. A temporary probe electrode is temporarily positioned adjacent to the nerve and at a location which is caudorostrally separate to the desired implantation location of the electrode array. The implanted position of the probe electrode is temporarily fixed relative to the nerve. During implantation of the electrode array, electrical stimuli are applied from one of the temporarily fixed probe electrode and the electrode array, to evoke compound action potentials on the nerve. Compound action potentials evoked by the stimuli are sensed from at least one electrode of the other of the temporarily fixed probe electrode and the electrode array. From the sensed compound action potentials a position of the electrode array relative to the nerve is determined.

16 Claims, 14 Drawing Sheets

Related U.S. Application Data continuation of application No. 15/535,014, filed as application No. PCT/AU2015/050753 on Nov. 30, 2015, now Pat. No. 10,588,698.

(51) Int. Cl.

| | | |
|---|---|---|
| A61B 5/388 | (2021.01) | |
| A61B 34/20 | (2016.01) | |
| A61N 1/05 | (2006.01) | |
| A61N 1/36 | (2006.01) | |
| A61N 1/372 | (2006.01) | |
| A61B 5/11 | (2006.01) | |

(52) U.S. Cl.
CPC .............. *A61B 5/686* (2013.01); *A61B 34/20* (2016.02); *A61N 1/0553* (2013.01); *A61N 1/3614* (2017.08); *A61N 1/36185* (2013.01); *A61N 1/372* (2013.01); *A61B 5/1118* (2013.01); *A61B 5/4029* (2013.01); *A61B 2034/2053* (2016.02); *A61B 2505/05* (2013.01); *A61B 2562/046* (2013.01); *A61N 1/36071* (2013.01)

(58) Field of Classification Search
CPC ......... A61B 5/24; A61B 5/388; A61B 5/4029; A61B 5/407; A61B 5/4893; A61B 5/686; A61N 1/0553; A61N 1/36071; A61N 1/3614; A61N 1/36185; A61N 1/372
See application file for complete search history.

(56) References Cited

U.S. PATENT DOCUMENTS

| | | | |
|---|---|---|---|
| 5,895,416 | A | 4/1999 | Barreras et al. |
| 6,516,227 | B1 | 2/2003 | Meadows et al. |
| 6,895,280 | B2 | 5/2005 | Meadows et al. |
| 6,909,917 | B2 | 6/2005 | Woods et al. |
| 7,177,675 | B2 | 2/2007 | Suffin et al. |
| 7,206,640 | B1 | 4/2007 | Overstreet |
| 7,634,315 | B2 | 12/2009 | Chelette |
| 7,890,182 | B2 | 2/2011 | Parramon et al. |
| 7,894,905 | B2 | 2/2011 | Pless et al. |
| 8,083,685 | B2 | 12/2011 | Fagin et al. |
| 8,249,698 | B2 | 8/2012 | Mugler et al. |
| 8,332,047 | B2 | 12/2012 | Libbus et al. |
| 8,515,545 | B2 | 8/2013 | Trier |
| 8,682,447 | B2 | 3/2014 | Bradley et al. |
| 9,044,155 | B2 | 6/2015 | Strahl |
| 9,067,074 | B2 | 6/2015 | Polefko et al. |
| 9,079,018 | B2 | 7/2015 | Olsen |
| 9,174,048 | B2 | 11/2015 | Polefko et al. |
| 9,358,390 | B2 | 6/2016 | Polefko et al. |
| 9,381,357 | B2 | 7/2016 | Min et al. |
| 9,572,986 | B2 | 2/2017 | Moffitt |
| 10,206,596 | B2 | 2/2019 | Single et al. |
| 10,500,399 | B2 | 12/2019 | Single |
| 10,568,559 | B2 | 2/2020 | Parker et al. |
| 10,588,524 | B2 | 3/2020 | Single et al. |
| 10,588,698 | B2 | 3/2020 | Parker et al. |
| 10,632,307 | B2 | 4/2020 | Parker |
| 10,842,996 | B2 | 11/2020 | Baru et al. |
| 10,849,525 | B2 | 12/2020 | Parker et al. |
| 10,894,158 | B2 | 1/2021 | Parker |
| 10,918,872 | B2 | 2/2021 | Parker et al. |
| 11,006,846 | B2 | 5/2021 | Parker et al. |
| 11,006,857 | B2 | 5/2021 | Parker |
| 11,045,129 | B2 | 6/2021 | Parker et al. |
| 11,110,270 | B2 | 9/2021 | Parker et al. |
| 11,135,424 | B2 | 10/2021 | Bradley et al. |
| 11,167,129 | B2 | 11/2021 | Parker |
| 11,172,864 | B2 | 11/2021 | Parker et al. |
| 11,179,091 | B2 | 11/2021 | Karantonis et al. |
| 11,191,966 | B2 | 12/2021 | Wah |
| 11,589,810 | B2 | 2/2023 | Gerber et al. |
| 2003/0153959 | A1 | 8/2003 | Thacker et al. |
| 2004/0116978 | A1 | 6/2004 | Bradley |
| 2005/0107674 | A1 | 5/2005 | Parthasarathy et al. |
| 2005/0216064 | A1 | 9/2005 | Heruth et al. |
| 2007/0225765 | A1 | 9/2007 | King |
| 2008/0132964 | A1 | 6/2008 | Cohen et al. |
| 2009/0030337 | A1 | 1/2009 | Gozani et al. |
| 2009/0058635 | A1 | 3/2009 | Lalonde et al. |
| 2009/0306533 | A1 | 12/2009 | Rousche et al. |
| 2010/0057159 | A1 | 3/2010 | Lozano |
| 2010/0100153 | A1 | 4/2010 | Carlson et al. |
| 2011/0077712 | A1 | 3/2011 | Killian |
| 2011/0130802 | A1 | 6/2011 | Libbus et al. |
| 2012/0059275 | A1 | 3/2012 | Fagin et al. |
| 2012/0101826 | A1 | 4/2012 | Visser et al. |
| 2012/0109004 | A1 | 5/2012 | Cadwell |
| 2012/0155183 | A1 | 6/2012 | Aritome |
| 2012/0185020 | A1 | 7/2012 | Simon et al. |
| 2012/0245481 | A1 | 9/2012 | Blanco et al. |
| 2012/0310301 | A1 | 12/2012 | Bennett et al. |
| 2013/0041449 | A1 | 2/2013 | Cela et al. |
| 2014/0046407 | A1 | 2/2014 | Ben-Ezra et al. |
| 2014/0249396 | A1 | 9/2014 | Shacham-diamand et al. |
| 2014/0277267 | A1 | 9/2014 | Vansickle et al. |
| 2014/0324118 | A1 | 10/2014 | Simon et al. |
| 2014/0350634 | A1 | 11/2014 | Grill et al. |
| 2015/0025597 | A1 | 1/2015 | Surth et al. |
| 2015/0051637 | A1 | 2/2015 | Osorio |
| 2015/0126839 | A1 | 5/2015 | Li et al. |
| 2015/0148869 | A1 | 5/2015 | Dorval, II et al. |
| 2016/0082265 | A1 | 3/2016 | Moffitt et al. |
| 2016/0082268 | A1 | 3/2016 | Hershey et al. |
| 2016/0101289 | A1 | 4/2016 | Stolen et al. |
| 2016/0106980 | A1 | 4/2016 | Surth et al. |
| 2016/0121124 | A1 | 5/2016 | Johanek et al. |
| 2016/0144189 | A1 | 5/2016 | Bakker et al. |
| 2016/0367808 | A9 | 12/2016 | Simon et al. |
| 2017/0173335 | A1 | 6/2017 | Min et al. |
| 2017/0173341 | A1 | 6/2017 | Johanek et al. |
| 2018/0071513 | A1 | 3/2018 | Weiss et al. |
| 2018/0104493 | A1 | 4/2018 | Doan et al. |
| 2018/0228547 | A1 | 8/2018 | Parker |
| 2019/0001139 | A1 | 1/2019 | Mishra et al. |
| 2019/0015663 | A1 | 1/2019 | Bennett et al. |
| 2019/0030339 | A1 | 1/2019 | Baru et al. |
| 2019/0125269 | A1 | 5/2019 | Markovic et al. |
| 2019/0142325 | A1 | 5/2019 | Min et al. |
| 2019/0357788 | A1 | 11/2019 | Single |
| 2020/0029914 | A1 | 1/2020 | Single |
| 2020/0129108 | A1 | 4/2020 | Parker et al. |
| 2020/0215331 | A1 | 7/2020 | Single |
| 2020/0282208 | A1 | 9/2020 | Parker |
| 2021/0001133 | A1 | 1/2021 | Williams et al. |
| 2021/0008373 | A1 | 1/2021 | Single et al. |
| 2021/0016091 | A1 | 1/2021 | Parker et al. |
| 2021/0106829 | A1 | 4/2021 | Bennett et al. |
| 2021/0121696 | A1 | 4/2021 | Parker et al. |
| 2021/0162214 | A1 | 6/2021 | Parker |
| 2021/0205613 | A1 | 7/2021 | Bradley et al. |
| 2021/0267518 | A1 | 9/2021 | Parker et al. |
| 2021/0308449 | A1 | 10/2021 | Parker |
| 2021/0315502 | A1 | 10/2021 | Parker et al. |
| 2021/0379386 | A1 | 12/2021 | Parker et al. |
| 2021/0387005 | A1 | 12/2021 | Parker et al. |
| 2021/0387008 | A1 | 12/2021 | Single |
| 2021/0393964 | A1 | 12/2021 | Single et al. |
| 2022/0007987 | A1 | 1/2022 | Huang et al. |
| 2022/0039724 | A1 | 2/2022 | Parker et al. |
| 2023/0248975 | A1 | 8/2023 | Bennett et al. |

FOREIGN PATENT DOCUMENTS

| | | |
|---|---|---|
| CN | 103648583 | 3/2014 |
| CN | 103654762 | 3/2014 |
| CN | 103842022 | 6/2014 |
| CN | 104411360 | 3/2015 |
| EP | 1244496 | 10/2002 |
| EP | 2520327 | 11/2012 |

(56) References Cited

FOREIGN PATENT DOCUMENTS

| | | |
|---|---|---|
| EP | 3229893 | 10/2017 |
| JP | 2006504494 | 2/2006 |
| JP | 2009512505 | 3/2009 |
| JP | 2013500779 | 1/2013 |
| JP | 2014522261 | 9/2014 |
| JP | 2014523261 | 9/2014 |
| WO | WO2000002623 A1 | 1/2000 |
| WO | 2002082982 | 10/2002 |
| WO | 2005122887 | 12/2005 |
| WO | WO2006107848 A3 | 12/2006 |
| WO | 2007050657 | 5/2007 |
| WO | WO2008030275 A1 | 3/2008 |
| WO | WO2008134059 A1 | 11/2008 |
| WO | WO2009042379 A1 | 4/2009 |
| WO | WO2009148425 A1 | 12/2009 |
| WO | 2010051406 | 5/2010 |
| WO | WO2010065146 A9 | 6/2010 |
| WO | WO2010065379 A1 | 6/2010 |
| WO | 2010124139 | 10/2010 |
| WO | WO2010138915 A1 | 12/2010 |
| WO | 2011014570 | 2/2011 |
| WO | 2011017778 | 2/2011 |
| WO | WO2011025979 A1 | 3/2011 |
| WO | WO2011053432 A1 | 5/2011 |
| WO | 2012016138 | 2/2012 |
| WO | WO2011159688 A3 | 3/2012 |
| WO | WO2012044695 A3 | 10/2012 |
| WO | 2012162349 | 11/2012 |
| WO | WO2013003368 A1 | 1/2013 |
| WO | WO2013052706 A1 | 4/2013 |
| WO | WO2013090675 A1 | 6/2013 |
| WO | 2013116161 | 8/2013 |
| WO | WO2013154758 A1 | 10/2013 |
| WO | 2014150001 | 9/2014 |
| WO | WO2014143577 A1 | 9/2014 |
| WO | WO2014145146 A1 | 9/2014 |
| WO | 2016048974 | 3/2016 |
| WO | 2016059556 | 4/2016 |
| WO | 2016168798 | 10/2016 |
| WO | 2017053504 | 3/2017 |
| WO | 2017210352 | 12/2017 |
| WO | 2018119220 | 6/2018 |
| WO | 2018160992 | 9/2018 |
| WO | 2019178634 | 9/2019 |
| WO | 2019204884 | 10/2019 |
| WO | 2019231796 | 12/2019 |
| WO | 2020082118 | 4/2020 |
| WO | 2020082126 | 4/2020 |
| WO | 2020082128 | 4/2020 |
| WO | 2020087123 | 5/2020 |
| WO | 2020087135 | 5/2020 |
| WO | 2021007615 | 1/2021 |

OTHER PUBLICATIONS

Gorman et al., "ECAP Mapping of the Spinal Cord: Influence of Electrode Position on AB Recruitment", (2012)., In 16th Annual Meeting. Presented at the North American Neuromodulation Society, Las Vegas, NV, 2 pgs.
Hallstrom et al., "Distribution of lumbar spinal evoked potentials and their correlation with stimulation-induced paresthesiae", Electroencephalography and Clinical Neurophysiology, Mar.-Apr. 1991, vol. 80, No. 2, pp. 126-139, doi:10.1016/0168-5597(91)90150-V.
Penar et al., "Cortical Evoked Potentials Used for Placement of a Laminotomy Lead Array: A Case Report", Neuromodulation: Technology at the Neural Interface, accessed Apr. 19, 2011, doi: 10.1111/j.1525-1403.2011.00352.x.
Richter et al., "EMG and SSEP Monitoring During Cervical Spinal Cord Stimulation", Journal of Neurosurgical Review 2011, Southern Academic Press, 1(S1), 2011, pp. 61-63.
Yingling et al., "Use of Antidromic Evoked Potentials in Placement of Dorsal Cord Disc Electrodes", Applied Neurophysiology, 1986, vol. 49, pp. 36-41.

Harvey-Lynch, Inc., "Multibeam and Mobile LIDAR Solutions," 2014, 2 pages.
"Evoke 12C Percutaneous Leads", Saluda Medical, specifications available in the "Evoke Surgical Guide", version 6, http://www.saludamedical.com/manuals/, retrieved May 2017.
"Percutaneous Lead Kit", St. Jude Medical Clinician's Manual, Models 3143, 3146, 3149, 3153, 3156, 3159, 3183, 3186, 3189, published Sep. 2016, 24 pages.
Abra Rd et al., "A time-frequency blindsignal separation methodapplicable to underdetermined mixtures of dependent sources", Signal Processing 85 (2005) 1389-1403.
Australian Examination Report for Application No. 2019283936, Mailed Apr. 1, 2021, 7 pages.
Bratta et al., "Orderly Stimulation of Skeletal Muscle Motor Units with Tripolar Nerve Cuff Electrode", IEEE Transactions on Biomedical Engineering, vol. 36, No. 8, 1989.
Casey et al., "Separation of Mixed Audio Sources by Independent Subspace Analysis", Mitsubishi Electric Research Laboratories (2001).
Celestin et al., "Pretreatment Psychosocial Variables as Predictors of Outcomes Following Lumbar Surgery and Spinal Cord Stimulation: A Systematic Review and Literature Synthesis", American Academy of Pain Medicine, 2009, vol. 10, No. 4, pp. 639-653. doi: 10.1111/j.1526-4637. 2009. 00632 .X.
Cong et al., "A 32-channel modular bi-directional neural interface system with embedded DSP for closed-loop operation", 40th European Solid State Circuits Conference (ESSCIRC), 2014, pp. 99-102.
Connolly et al., "Towards a platform for prototyping control systems for optimization of neuromodulation therapies", IEEE Biomedical Circuits and Systems Conference (BioCAS), 2015, pp. 1-4.
Delgado et al., "Measurement and interpretation of electrokinetic phenomena", Pure Appl. Chem., 2005, vol. 77, No. 10, pp. 1753-1805.
Extended European Search Report for European Application 18910394.8 Search Completed Oct. 7, 2021, Mailed Oct. 15, 2021, 8 pgs.
Extended European Search Report for European Application No. 15789515.2, Search completed Dec. 4, 2017, Mailed Jan. 30, 2018, 7 Pgs.
Extended European Search Report for European Application No. 16802238.2, Mailed Jan. 14, 2022, 7 Pgs.
Extended European Search Report for European Application No. 17778477.4, report completed Nov. 12, 2019, mailed Nov. 20, 2019, 7 pgs.
Extended European Search Report for European Application No. 17814341.8, report completed Dec. 12, 2019, report mailed Jan. 2, 2020, 8 pgs.
Extended European Search Report for European Application No. 19793420.1, Search completed Dec. 6, 2021, Mailed Dec. 17, 2021, 9 Pgs.
Fitzpatrick et al., "A Nerve Cuff Design for the Selective Activation and Blocking of Myelinated Nerve Fibers", IEEE Engineering in Medicine and Biology Society, vol. 13, No. 2, 1991.
Howell et al., "Evaluation of Intradural Stimulation Efficiency and Selectivity in a Computational Model of Spinal Cord Stimulation", PLOS ONE, DO1:10.1371/journal.pone.0114938, Dec. 23, 2014.
International Preliminary Report for International Application No. PCT/AU2019/050384, Mailed Oct. 27, 2020, 8 pgs.
International Preliminary Report on Patentability for International Application No. PCT/AU2018/050278, Issued Sep. 29, 2020, 7 pgs.
International Search Report and Written Opinion for International Application No. PCT/AU2018/050278, Search completed Jun. 18, 2018, Mailed Jun. 18, 2018, 12 pgs.
International Search Report and Written Opinion for International Application No. PCT/AU2019/050384, Search completed Jun. 25, 2019, Mailed Jun. 25, 2019, 15 pgs.
International Search Report and Written Opinion for International Application No. PCT/AU2019/051385, Search completed Mar. 24, 2020, Mailed Mar. 24, 2020, 8 Pgs.
International Search Report and Written Opinion for International Application No. PCT/AU2020/050725, Search completed Oct. 19, 2020, Mailed Oct. 19, 2020, 8 Pgs.

(56) References Cited

OTHER PUBLICATIONS

International Search Report for International Application No. PCT/AU2019/051151, International Filing Date Oct. 22, 2019, Search Completed Feb. 24, 2020, Mailed Feb. 24, 2020, 9 pgs.
International Search Report for International Application No. PCT/AU2019/051160, International Filing Date Oct. 23, 2019, Search Completed Jan. 28, 2020, Mailed Jan. 28, 2020, 13 pgs.
International Search Report for International Application No. PCT/AU2019/051163, International Filing Date Oct. 23, 2019, Search Completed Jan. 21, 2020, Mailed Jan. 31, 2020, 8 pgs.
International Search Report for International Application No. PCT/AU2019/051197, International Filing Date Oct. 30, 2019, Search Completed Jan. 21, 2020, Mailed Jan. 21, 2020, 15 pgs.
International Search Report for International Application No. PCT/AU2019/051210, International Filing Date Nov. 2, 2019, Search Completed Feb. 4, 2020, Mailed Feb. 4, 2020, 10 pgs.
Jang et al, "Single Channel Signal Separation Using Time-Domain Basis Functions", IEEE Signal Processing Letters, Jun. 2003, vol. 10, No. 6.
Jang et al., "A Maximum Likelihood Approach to Single-channel Source Separation", Journal of Machine Learning Research 4 (2003) 1365-1392.
Japanese Office Action for Application No. 2017-546830, Mailed Feb. 20, 2020, 5 pages with English translation.
Japanese Office Action for Application No. 2017-553090, Mailed Mar. 16, 2020, 12 pages with English translation.
Japanese Office Action for Application No. 2018-552138, Mailed Mar. 1, 2021, 7 pages with English translation.
Japanese Office Action for Application No. 2018-513699, Mailed Jun. 8, 2020, 7 pages with English translation.
Jones et al., "Scaling of Electrode-Electrolyte Interface Model Parameters In Phosphate Buffered Saline", IEEE Transactions on Biomedical Circuits and Systems, 2015, vol. 9, No. 3, pp. 441-448.
Kopelman et al., "Attempted Reversible Sympathetic Ganglion Block by An Implantable Neurostimulator", Interactive Cardiovascular and Thoracic Surgery, Feb. 7, 2012, vol. 14, Issue 5, pp. 605-609.
Laird-Wah, "Improving Spinal Cord Stimulation: Model-Based Approaches to Evoked Response Telemetry", UNSW, Aug. 2015.
Mannan et al., "Identification and Removal of Physiological Artifacts From Electroencephalogram Signals: A Review", IEEE Access, May 31, 2018, vol. 6, pp. 30630-30652, https://doi.org/10.1109/ACCESS.2018.2842082.
Niazy et al., "Removal of FMRI environment artifacts from EEG data using optimal basis sets", NeuroImage 28 (2005) 720-737.
North et al., "Prognostic value of psychological testing in patients undergoing spinal cord stimulation: a prospective study", Neurosurgery, Aug. 1, 1996, vol. 39, Issue 2, pp. 301-311. https://doi.org/10.1097/00006123-199608000-00013.
Office Action for Chinese Patent Application No. 201680020725.4, dated Mar. 16, 2020, 8 pgs.
Parker et al., "Electrically evoked compound action potential recording in peripheral nerves", Bioeletron. Med., vol. 1, No. 1, 2018, pp. 71-83, ISSN 2059-1500.
Peterson et al., "Stimulation artifact rejection in closed-loop, distributed neural interfaces", ESSCIRC, 42nd European Solid-State Circuits Conference, Lausanne, 2016, pp. 233-235.
Rijkhoff et al., "Acute Animal Studies on the Use of Anodal Block to Reduce Urethral Resistance in Sacral Root Stimulation", IEEE Transactions on Rehabilitation Engineering, vol. 2, No. 2, 1994.
Rijkhoff et al., "Orderly Recruitment of Motoneurons in an Acute Rabbit Model", Annual International Conference of the IEEE Engineering in Medicine and Biology Society, vol. 20, No. 5, 1998.
Scott et al., "Compact Nonlinear Model of an Implantable Electrode Array for Spinal Cord Stimulation (SCS)", IEEE Transactions on Biomedical Circuits and Systems, 2014, vol. 8, No. 3, pp. 382-390.
Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.
Takahashi et al, "Classification of neuronal activities from tetrode recordings using independent component analysis", Neurocomputing, (2002), vol. 49, Issues 1-4, 289-298.
Zhang et al., "Automatic Artifact Removal from Electroencephalogram Data Based on A Priori Artifact Information", BioMed research international. 2015. 720450. Aug. 25, 2015 DOI: https://doi.org/10.1155/2015/720450.
Zhou et al., "A High Input Impedance Low Noise Integrated Front-End Amplifier for Neural Monitoring", IEEE Transactions on Biomedical Circuits and Systems, 2016, vol. 10, No. 6, pp. 1079-1086.

IMPLANTABLE ELECTRODE POSITIONING

CROSS-REFERENCE TO RELATED APPLICATIONS

This application is continuation of U.S. application Ser. No. 16/752,209, filed Jan. 24, 2020, which is a continuation of U.S. application Ser. No. 15/535,014, filed Jun. 9, 2017 and issued on Mar. 17, 2020 as U.S. Pat. No. 10,588,698, which is a national stage of Application No. PCT/AU 2015/050753, filed Nov. 30, 2015, which application claims the benefit of Australian Provisional Patent Application No. 2014905030 filed Dec. 11, 2014, the disclosures of which are incorporated herein by reference in their entireties.

TECHNICAL FIELD

The present invention relates to monitoring compound action potentials during surgery to assist with implantable electrode placement.

BACKGROUND OF THE INVENTION

A range of implanted neural devices exist, including: spinal cord implants which electrically stimulate the spinal column in order to suppress chronic pain; cochlear implants which electrically stimulate the auditory nerve to produce a hearing sensation; deep brain stimulators which electrically stimulate selected regions of the brain to treat conditions such as Parkinson's disease or epilepsy; and neural bypass devices which electrically stimulate either afferent sensory nerve fibres to reproduce impaired sensory function or efferent motor nerve fibres to reproduce impaired motor activity, or both.

Such devices require implantation of an electrode array proximal to the neural pathway of interest, in order to enable electrical stimuli to be delivered from the array to the nerve in order to evoke compound action potentials, or neural responses. For example, the typical procedure for implantation of a spinal cord stimulator having a paddle electrode involves placing the patient under general anaesthesia and performing a laminectomy or removal of part of the dorsal process to access the epidural space. However the success of spinal cord stimulation for pain relief, and of neural device implantation in general, is strongly linked to the accuracy of the placement of the implanted stimulating electrodes during surgery. Physiologic midline placement of paddle leads is important to avoid uncomfortable side-effects during stimulation as a result of the activation of dorsal root fibers. One approach to accurately position the electrode array is to temporarily wake the patient from the general anaesthesia and to ask the patient to report the location of paraesthesia produced by stimuli delivered by the array. Temporarily waking a patient from a general can be difficult, and even once the patient is awake the reports provided by a drowsy patient are often unreliable. Because the patient is not fully alert when temporarily awoken from general anaesthesia, and is otherwise asleep during the remainder of the implantation procedure, they can only provide limited feedback regarding the location of the paraesthesia, or regarding any complications arising from lead placement. Although complications are rare they can be very serious.

Another option is to not wake the patient during surgery, and to use anatomical targeting to guide the positioning of the electrode array, by reference to anatomical markers that can be imaged via fluoroscopy, instead of relying on unreliable patient feedback. However, fluoroscopic imaging resolution is relatively imprecise, compared to the accuracy requirements of lead placement. Moreover, complications of implanting a surgical lead while a patient is asleep can include damage to the spinal cord due to direct pressure of the lead as it is placed into the epidural space, or post-operative damage due to the development of a hematoma over the lead, which can then create pressure on the lead and damage the dorsal column axons.

Another situation requiring accurate electrode lead placement is the case of paddle leads, which comprise a two dimensional array of electrodes which when implanted into the epidural space extend both along (caudorostrally relative to) and across (mediolaterally relative to) the dorsal columns. Paddle leads for example can be used to treat patients with bilateral pain complaints, with the goal to provide paraesthesia to both sides of the body. To accomplish this it is preferable to place the paddle lead over the physiologic midline of the dorsal columns. However the physiologic midline, being the centre line of the spinal cord which demarcates between the fibres innervating the left side and the right side of the body, may or may not be well aligned with the anatomical midline as defined by anatomical markers that can be imaged via fluoroscopy. Consequently, implanting a patient under a general anaesthetic by reference to anatomical markers can result in the paddle electrode array not providing equal stimulation and paraesthesia to both sides of the body.

One technique for defining the physiologic midline is to use somatosensory potentials, observed from electrodes placed on the scalp. In this technique the stimulation of peripheral nerve fibres, such as stimulation of the posterior tibial nerve by needle electrode, evokes a response in the somatosensory cortex. By simultaneously stimulating dorsal column fibres using the spinal cord lead, a collision can be created between the peripherally evoked response and the spinally evoked response. This collision results in an observed depression of the somatosensory responses. Both tibial nerves are stimulated, so that a symmetric depression from left and right somatosensory cortex responses will indicate that the stimulated electrode is above the midline.

Somatosensory response to stimulation of peripheral nerves has also been used to identify the rostral caudal location of the electrode with respect to peripheral locations. However, this has been less successful as when considering a sensory homunculus the representation of the legs for example on the sensory cortex is small, and buried within the longitudinal fissure of the brain. Since many chronic pain patients have lower extremity pain this method has not proved to be useful. Another method has been to record motor evoked potentials from the muscles in the periphery in response to stimulation at the spinal cord. Although more successful at activating muscle fibres, dorsal column motor stimulation requires very high currents and as such does not closely correspond to the area of sensory activation.

The dorsoventral position of the electrode array is also of importance, as a large nerve-to-electrode distance can increase the stimulus power required to evoke neural responses and thus decrease battery life. A large electrode-to-nerve distance can also decrease the strength of observed neural signals reaching sense electrodes, in devices configured to measure the neural responses. On the other hand, bringing the electrode array too close to the nerve can apply pressure or direct trauma to the nerve and cause temporary or even permanent nerve damage. However, the dorsoventral position is also difficult to accurately determine during surgery. Occasionally a surgeon may take a lateral view image with fluoroscope, however these images are not of sufficient resolution to sufficiently accurately judge the proximity of the array to the cord.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method of surgically positioning an electrode array at a desired implantation location relative to a nerve, the method comprising:
  implanting a temporary probe electrode adjacent to the nerve and at a location which is caudorostrally separate to the desired implantation location of the electrode array;
  temporarily fixing the implanted position of the probe electrode relative to the nerve;
  during implantation of the electrode array, applying electrical stimuli from one of the temporarily fixed probe electrode and the electrode array, to evoke compound action potentials on the nerve;
  sensing, from at least one electrode of the other of the temporarily fixed probe electrode and the electrode array, the compound action potentials evoked by the stimuli; and
  determining from the sensed compound action potentials a position of the electrode array relative to the nerve.

According to a second aspect the present invention provides a system for positioning an electrode array at a desired implantation location relative to a nerve, the system comprising:
  a temporary probe electrode configured to be implanted adjacent to the nerve at a location which is caudorostrally separate to the desired implantation location of the electrode array, and configured to be temporarily fixed relative to the nerve while implanted;
  an electrode array configured to be implanted adjacent to the nerve at the desired implantation location, and comprising at least one electrode configured to evoke or sense compound action potentials; and
  a controller configured to:
    cause electrical stimuli to be applied from one of the temporarily fixed probe electrode and the electrode array to evoke compound action potentials on the nerve during implantation of the electrode array;
    sense from at least one electrode of the other of the temporarily fixed probe electrode and the electrode array the compound action potentials evoked by the stimuli; and determine from the sensed compound action potentials a position of the electrode array relative to the nerve.

A non-transitory computer readable medium for surgically positioning an electrode array at a desired implantation location relative to a nerve, comprising instructions which, when executed by one or more processors, causes performance of the following:
  computer program code means for, during implantation of the electrode array, applying electrical stimuli from one of the electrode array and a probe electrode which is temporarily fixed adjacent to the nerve at a location which is caudorostrally separate to the desired implantation location of the electrode array, to evoke compound action potentials on the nerve;
  computer program code means for sensing, from at least one electrode of the other of the electrode array and the probe electrode, the compound action potentials evoked by the stimuli; and
  computer program code means for determining from the sensed compound action potentials a position of the electrode array relative to the nerve.

In some embodiments of the invention, the probe electrode is surgically introduced via the same incision as the electrode array. In some such embodiments the probe electrode may be fed from the incision in a first caudorostral direction which is opposite to a second caudorostral direction in which the electrode array is introduced. In further such embodiments, in which the nerve is the dorsal column, the probe electrode may be temporarily fixed so as to be positioned in the same or a nearby vertebral segment as the electrode array. Temporarily fixing the probe electrode near the electrode array, such as in the same vertebral segment or in an adjacent vertebral segment, or nearby within a small number of vertebral segments, is desirable because while the fibres of the dorsal column run approximately parallel over the distances of a few vertebral segments, any twist or rotation of or within the spinal cord could produce a misalignment of the electrophysiological midline relative to the anatomical midline and this risk rises beyond a few vertebral segments, and this might alter or make unclear the spatial representation of the physiological midline of the nerve which is provided by the ECAPs when first evoked. Temporarily fixing the probe electrode near the electrode array is also advantageous when it permits a single surgical incision to be used, such as a single laminectomy, to implant both the probe electrode and the electrode array.

In some embodiments of the invention, the desired positioning of the electrode array is relative mediolaterally to a physiologic midline of the nerve. For example, the desired mediolateral positioning of the electrode array may be centrally over the midline of the nerve. In such embodiments the probe electrode is preferably configured to simultaneously stimulate an even distribution of fibres mediolaterally across the nerve. This may be achieved by the probe electrode comprising a wide electrode element, or a plurality of electrode elements, which extend(s) across substantially an entire mediolateral extent of the nerve, and/or by applying probe stimuli which are sufficiently large, such as being a multiple of 1.5, two or more of the threshold stimulus level, so as to evoke responses in most or all fibres of the nerve. In such embodiments the probe electrode thus launches a compound action potential along the fibres of the nerve which is substantially electrically centred on the nerve, even though the probe electrode itself will not necessarily be precisely centrally positioned. Identification of the physiologic midline of the nerve, and positioning of the electrode array relative to the identified midline, may then be achieved by providing two laterally spaced apart sense electrodes on the electrode array, and monitoring a relative strength of the compound action potential sensed by each of the sense electrodes. If one sense electrode senses a stronger compound action potential, that electrode is likely closer to the physiologic midline and the electrode array can be mediolaterally moved by the surgeon accordingly. If the sense electrodes sense equally strong CAPs, they are likely equidistant mediolaterally from, i.e. centrally positioned over, the physiologic midline of the nerve.

In additional or alternative embodiments of the invention a radial spacing of the electrode array from the nerve, such as a dorsoventral position of a dorsal column stimulator, may be determined. In such embodiments, the probe electrode preferably comprises first and second stimulus electrodes each at distinct radii away from the nerve. For example where the probe electrode comprises a sheet substrate, first and second electrodes may be formed on opposing outer surfaces of the sheet and may thereby be positioned at radii from the nerve which differ by the thickness of the sheet. The first and second probe electrodes may then be used to deliver stimuli of equal intensity, at different times. A sense electrode of the electrode array being implanted is then used to sense a first intensity of the CAP evoked by the first probe electrode, and a second intensity of the CAP evoked by the second probe electrode. A difference between the first intensity and the second intensity may then be used to estimate a radial spacing of the electrode array from the nerve. Notably, even though a height of the probe electrode above the nerve may not be known, such embodiments permit a relative height of the electrode array to be monitored by comparing the first and second intensity measurements over time as the electrode array is moved during implantation.

The probe electrode may comprise multiple elements which are caudorostrally spaced apart along the nerve, for example to facilitate embodiments in which the probe electrode senses ECAPs evoked by the electrode array, and/or to enable an optimally caudorostrally positioned probe electrode element to be selected in order to maximise recruitment and or measurement sensitivity.

Because the ECAPs produced by the probe electrode are being used as a point of reference during ongoing positioning of the electrode array, the probe electrode needs to be in a fixed location throughout the procedure. The probe electrode may be fixed by being temporarily anchored upon a vertebra, within the epidural space. Alternatively the probe electrode may be fixed to an external structure such as a surgical stabilising arm and have suitable longitudinal rigidity to maintain a substantially constant implanted position relative to the nerve for the duration of the procedure, or may be fixed by any other suitable temporary fixing means.

In some embodiments of the invention the probe electrode is a peripheral nerve stimulator delivering stimuli to evoke CAPs on peripheral nerve(s) at a location of interest such as a desired site of paraesthesia. In some such embodiments, the electrode array which is being implanted may comprise both stimulus electrodes and sense electrodes, whereby an array location at which the sense electrodes sense a maximal collision of CAPs evoked by the stimulus electrodes with the CAPs evoked by the peripheral nerve stimulator is taken to be an optimal caudorostral position of the stimulus electrodes relative to the location of interest. Collision of CAPs, being the reduced recruitment achieved by a given stimulus due to some or all of the adjacent population of fibres being in their refractory period because of the peripherally evoked CAP, may be determined by a depression in the overall amplitude of sensed CAPs. Preferably the timing of the delivery of the dorsal column pulse is adjusted to uniquely detect collision.

The present invention thus recognises that sensing compound action potentials by use of electrodes of an electrode array, can be used to monitor the placement of the electrode array during surgery. The present invention thus provides a method to better assess the position of the electrode array, in the dorsoventral, caudorostral and/or mediolateral direction, quickly and simply while the patient is under general anaesthesia, without requiring scalp electrodes for somatosensory cortex monitoring, for example.

It is to be appreciated that embodiments of the present invention may be implemented in respect of any suitable neurostimulator such as spinal cord stimulators, cardiac pacemakers/defibrillators, functional electrical stimulators (FES), pain stimulators, etc.

The stimuli may be delivered by the probe electrode, and evoked ECAPs may be sensed by the electrode array. Alternatively, the stimuli may be delivered by the electrode array, and evoked ECAPs may be sensed by the probe electrode, and it is to be understood that in all embodiments described herein the positioning roles of the probe electrode and the electrode array may be reversed, within the scope of the present invention. Moreover, over time the source of stimuli may alternate between the probe electrode and the electrode array, which may assist with position resolution.

BRIEF DESCRIPTION OF THE DRAWINGS

An example of the invention will now be described with reference to the accompanying drawings, in which:

FIG. 6b shows ECAP signals recorded from the arrangement of FIG. 6a;

DESCRIPTION OF THE PREFERRED EMBODIMENTS

Figure 1:
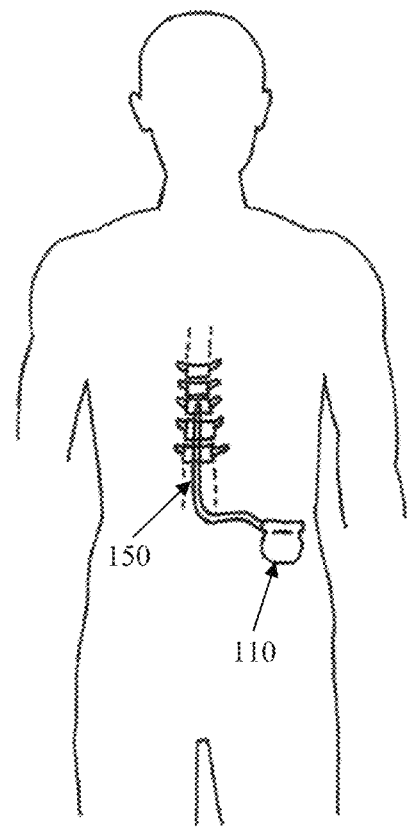
FIG. 1 schematically illustrates an implanted spinal cord stimulator.

FIG. 1 schematically illustrates an implanted spinal cord stimulator 100. Stimulator 100 comprises an electronics module 110 implanted at a suitable location in the patient's abdomen and an electrode assembly 150 implanted within the epidural space and connected to the module 110 by a suitable lead.

Figure 2:
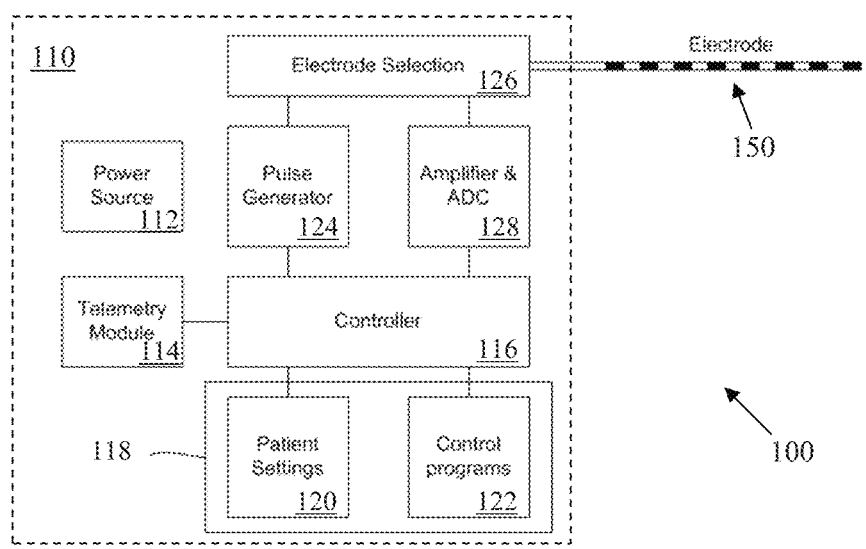
FIG. 2 is a block diagram of the implanted neurostimulator.

FIG. 2 is a block diagram of the implanted neurostimulator 100. Module 110 contains a battery 112 and a telemetry module 114. In embodiments of the present invention, any suitable type of transcutaneous communication, such as infrared (IR), electromagnetic, capacitive and inductive transfer, may be used by telemetry module 114 to transfer power and/or data between an external device and the electronics module 110.

Module controller 116 has an associated memory 118 storing patient settings 120, control programs 122 and the like. Controller 116 controls a pulse generator 124 to generate stimuli in the form of current pulses in accordance with the patient settings 120 and control programs 122. Electrode selection module 126 switches the generated pulses to the appropriate electrode(s) of electrode array 150, for delivery of the current pulse to the tissue surrounding the selected electrode. Measurement circuitry 128 is configured to capture measurements of neural responses sensed at sense electrode(s) of the electrode array as selected by electrode selection module 126.

Figure 3:
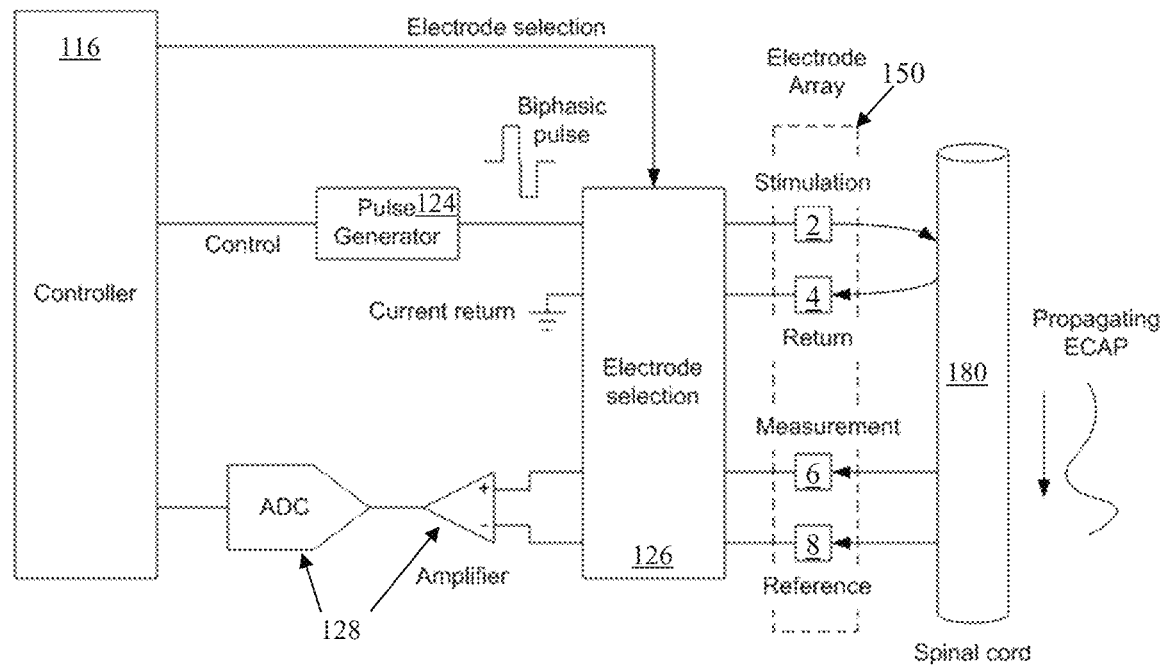
FIG. 3 is a schematic illustrating interaction of the implanted stimulator with a nerve.

FIG. 3 is a schematic illustrating interaction of the implanted stimulator 100 with a nerve 180, in this case the spinal cord. Electrode selection module 126 selects a stimulation electrode 2 of electrode array 150 to deliver a current pulse to surrounding tissue including nerve 180, and also selects a return electrode 4 of the array 150 for current recovery to maintain a zero net charge transfer.

Delivery of an appropriate stimulus to the nerve 180 evokes a neural response comprising a compound action potential which will propagate along the nerve 180 as illustrated, for therapeutic purposes which in the case of spinal cord stimulator for chronic pain is to create paraesthesia at a desired location.

The device 100 is further configured to sense the existence and intensity of compound action potentials (CAPs) propagating along nerve 180, whether such CAPs are evoked by the stimulus from electrodes 2 and 4, or otherwise evoked. To this end, any electrodes of the array 150 may be selected by the electrode selection module 126 to serve as measurement electrode 6 and measurement reference electrode 8. Signals sensed by the measurement electrodes 6 and 8 are passed to measurement circuitry 128, which for example may operate in accordance with the teachings of International Patent Application Publication No. WO2012155183 by the present applicant, the content of which is incorporated herein by reference.

Figure 4:
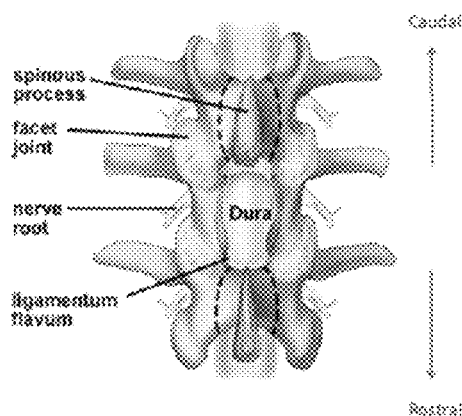
FIG. 4 is a view of the spinal cord through a conventional laminectomy.

FIG. 4 is a view of the spinal cord through a conventional laminectomy. Some embodiments provide for insertion of a probe electrode through such a surgical incision and in the caudal direction within the epidural space, and the simultaneous implantation of an electrode array through the same incision and then in the rostral direction within the epidural space.

Referring to FIG. 4, the lamina is a posterior arch of the vertebral bone lying between the spinous process (which juts out in the middle) and the more lateral pedicles and the transverse processes of each vertebra. The pair of laminae, along with the spinous process, make up the posterior wall of the bony spinal canal. A conventional laminectomy involves excision of the posterior spinal ligament and some or all of the spinous process. Removal of these structures with an open technique requires disconnecting the many muscles of the back attached to them. After the laminectomy is performed the electrode is then positioned in place with forceps or other tool by sliding the electrode in the rostral direction into the epidural space. Conventionally, direct visual or radiographic examination is used to determine the position of the electrode.

Figure 5A:
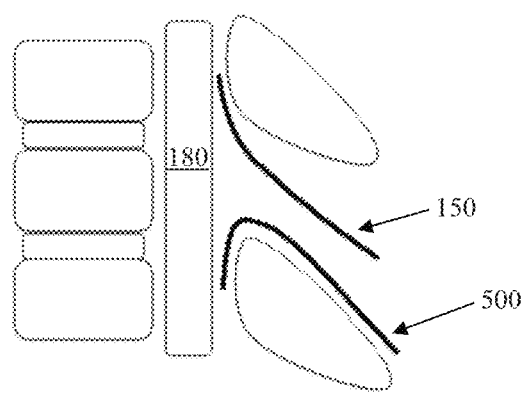
FIG. 5a illustrates a probe electrode, and an electrode array being positioned.

The arrangement shown in FIG. 5a separates the probe electrode from the recording electrode. The probe electrode can be arranged on a surgical tool, which can be positioned over the dorsal column and, importantly, kept stationary while the recording electrode is moved. The probe electrode may be placed caudally or rostrally of the electrode array. The probe electrode(s) are designed to stimulate a large area of the cord and are temporarily placed at the time of surgery.

Figure 5B:
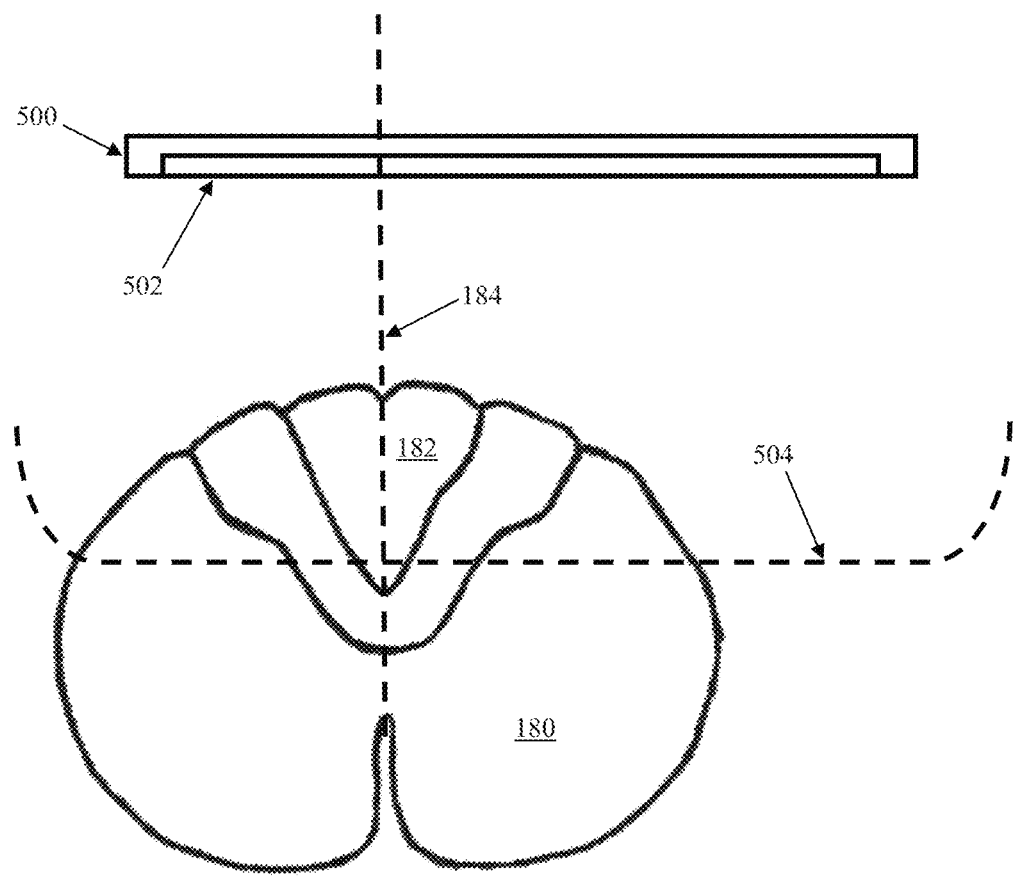
FIG. 5b illustrates the probe electrode evoking a neural response.
Figure 5C:
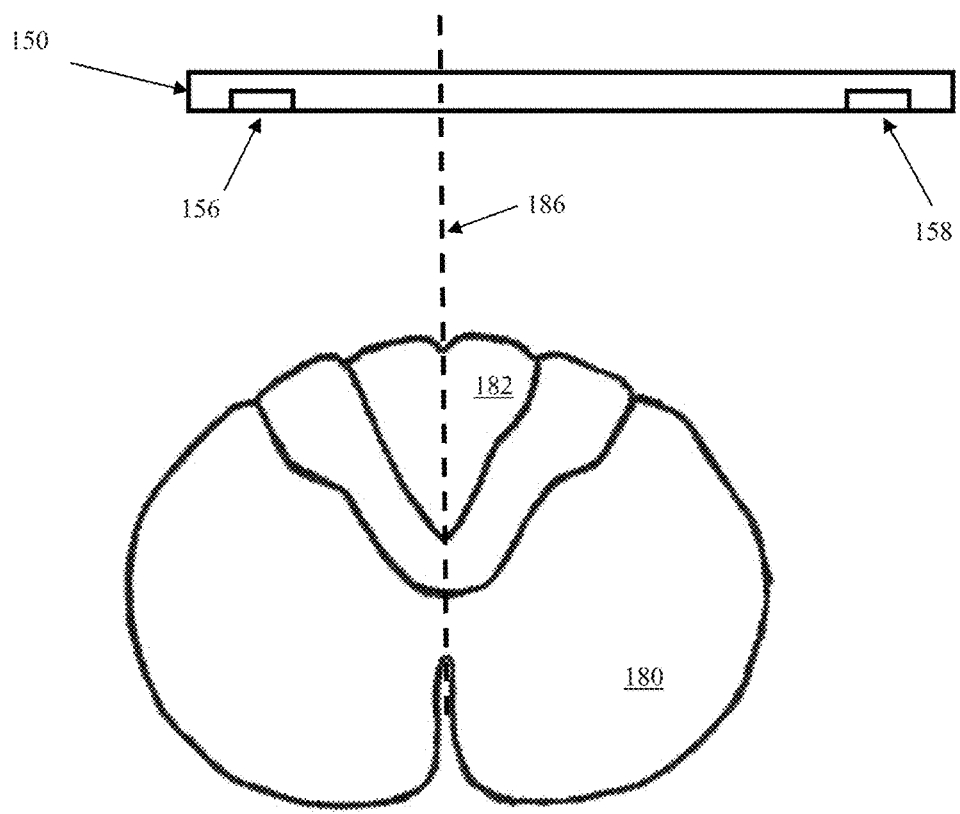
FIG. 5c illustrates measurement of the evoked response to locate the physiologic midline of the nerve, in accordance with a first embodiment of the invention.

FIGS. 5a-5c illustrate such an arrangement. In FIG. 5a the electrode array 150 is inserted rostrally, while probe electrode 500 is inserted caudally. The probe electrode 500 is preferably attached to a handle on surgical tool to allow for simple placement. The insertion tool(s) used allow both the electrode array and the probe electrode to be placed with a relatively steep angle of surgical approach through a shared incision. Such an approach can be achieved by performing a standard surgical laminectomy or using a surgical tubular retractor system, such as the MetRX or the Swivel retractor, modified if required to provide appropriate guides and anchors to facilitate the placement of both the probe electrode and the insertion tool for the SCS electrode.

In other embodiments, percutaneous implantation of a paddle lead may be performed, as follows. A standard 14 gauge tuohy needle is used to access the epidural space. A guide wire is then inserted through the needle to allow access to the epidural space. The standard needle is then removed; a custom needle is then passed over the guide wire with the tip just entering the epidural space. The tip has a sleeve to prevent coring of the tissue. The guide wire and sleeve are removed allowing the custom paddle lead to pass into the epidural space. As the folded lead enters the epidural space it is separated to allow it to unfurl and lie flat over the dorsal columns. A stylet is used to help position the lead.

As shown in the cross sectional view of FIG. 5b, probe electrode 500 comprises an electrode element 502 which extends widely in the mediolateral direction relative to the spinal cord 180. Further, a stimulus intensity delivered by the probe electrode element 502 is set to be significantly above a stimulus threshold. The stimulus threshold for the recording of ECAPs on the electrode array 150 can be identified in accordance with any suitable technique. Delivery of a sufficiently large stimulus from element 502 will create a region of recruitment 504 which is sufficiently large to recruit action potentials within most if not all of the ascending fibres of the dorsal column 182. As can be seen the wide extent of element 502 means that, even though the probe electrode 500 and the associated region of recruitment 504 will not necessarily be centrally positioned about the physiologic midline 184 of the spinal cord 180, most if not all of the ascending fibres of the dorsal column 182 will nevertheless be recruited. It is to be appreciated that any other configurations of the probe electrode which achieve a corresponding effect are within the scope of the present invention.

Because probe electrode 500 has been inserted caudally of electrode array 150 in the manner shown in FIG. 5*a*, the orthodromic rostral propagation of the compound action potential evoked by a single stimulus delivered by probe electrode 500 will take such an action potential past electrode array 150. Alternative embodiments may position the probe electrode 500 rostrally of the electrode array 150, and exploit antidromic caudal propagation of the compound action potential along the dorsal column 182 from the probe electrode 500 to the electrode array 150.

Once again, due to the difficulties of accurate implantation, electrode array 150 will not necessarily be centrally positioned over the physiologic midline 186 of the spinal cord 180. It is further noted that that midline 186 at the location of the array 150 may or may not align precisely with the midline 184 at the location of probe 500.

The compound action potential evoked by the probe electrode 500 propagates rostrally within the dorsal column 182 and passes electrode array 150, as shown in the cross sectional view of FIG. 5*c*, where it is simultaneously sensed by sense electrodes 156 and 158. Because most if not all of the ascending fibres of the dorsal column 182 have been recruited by probe electrode 500, the electric field of the compound action potential can be considered to be centrally located on the physiologic midline 186. Consequently, a first field strength of the compound action potential sensed by sense electrode 156 depends on the distance of the sense electrode 156 from the midline 186, and a second field strength of the compound action potential sensed by sense electrode 158 depends on the distance of the sense electrode 158 from the midline 186. The first field strength and second field strength may then be compared to determine which sense electrode is closer to the midline 186, and an indication may be given to a surgeon as to which direction mediolaterally the array 150 should be moved in order to improve the position of the array during surgery.

The above described actions can then be incorporated into an implantation process, as follows:
1. Surgical approach and placement of the probe electrode 500;
2. Insertion of the tip of the electrode array 150 and connection of the array 150 to the recording system;
3. Stimulation amplitude adjustment of the probe electrode 500 by increasing the amplitude, until the threshold for ECAP generation is reached, as measured by the electrodes on the inserted tip of array 150. The amplitude is further increased to be 1.5× or 2× the threshold current;
4. The electrode array 150 is then further inserted in the epidural space by manipulation with forceps or other appropriate surgical tool;
5. The amplitude of the ECAPS is continuously monitored and displayed. The implanting surgeon manipulates the electrode to achieve a balance of ECAP amplitudes from electrodes on opposing lateral sides of the electrode array 150.
6. When the left and right most lateral electrodes 156 and 158 are producing the same amplitude ECAP responses, the electrode array 150 is aligned with the electrophysiological midline.

Figure 5D:
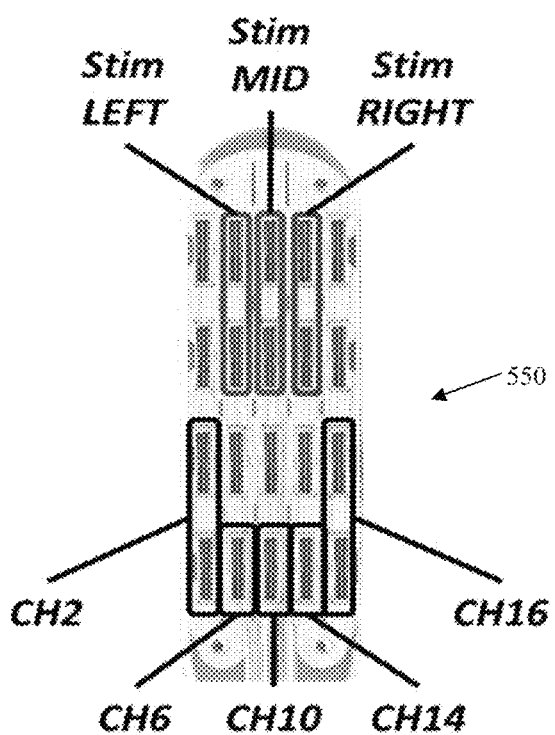
FIGS. 5d-5f illustrate experimental verification of the principles of FIGS. 5a-5c.
Figure 5E:
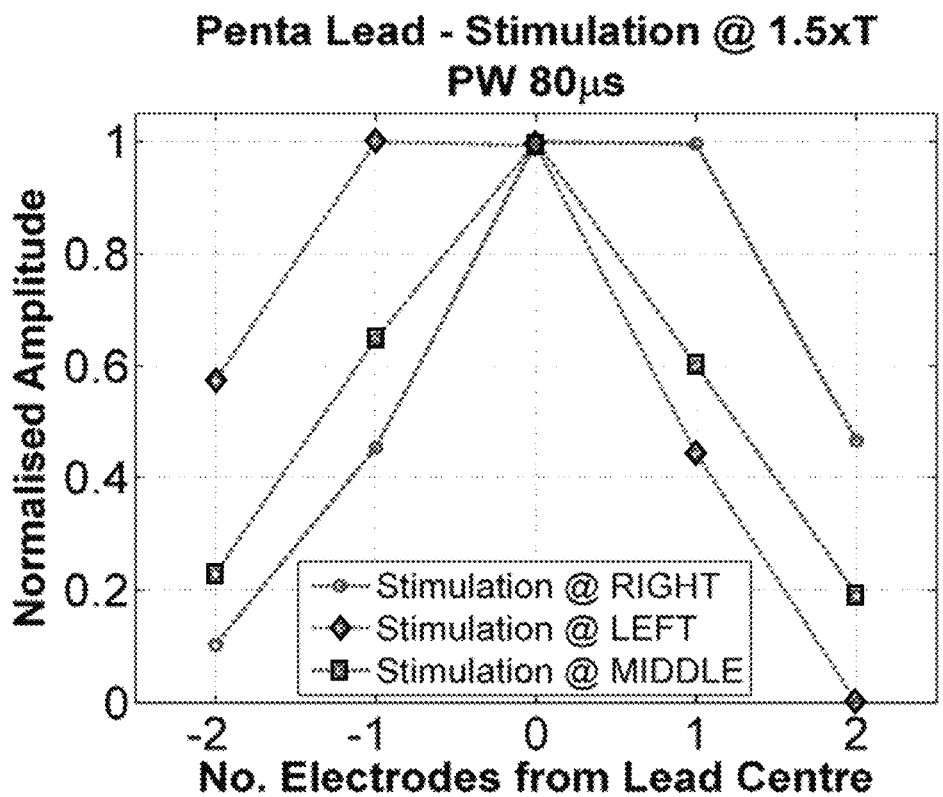
Figure 5F:
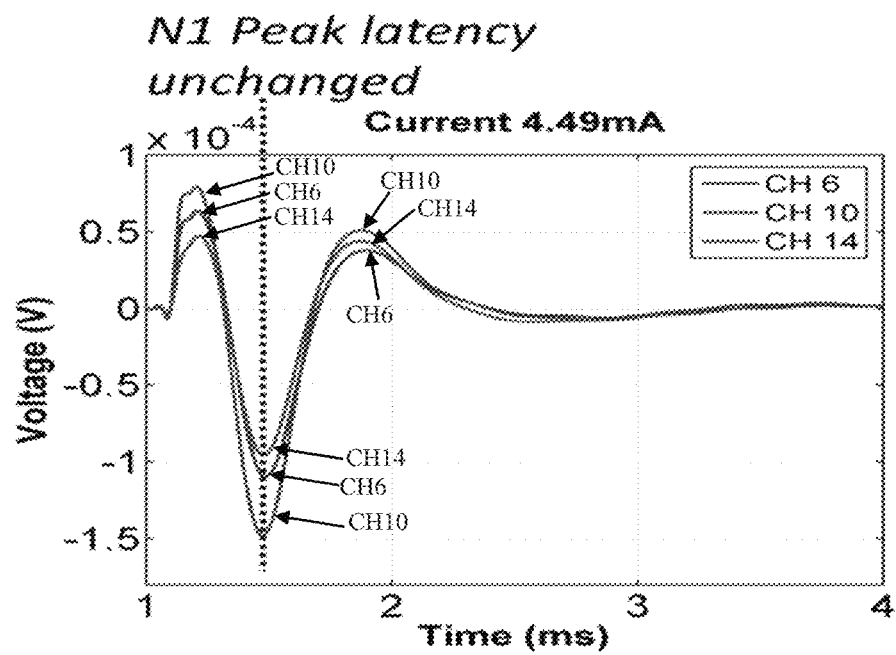

FIGS. 5*d* and 5*e* illustrate experimental verification of the principles of FIGS. 5*a*-5*c*. Data was obtained from a patient implanted with a St Jude Penta™ lead 550 shown in FIG. 5*d*. FIG. 5*e* shows that the amplitude of the ECAPs recorded on the electrodes in line with the stimulation were larger compared to those on either side (more lateral), while FIG. 5*f* shows that the latency of the N1 peaks remained the same. FIGS. 5*d*-5*f* further illustrate that the electrically evoked compound action potential can be used to locate the midline of the dorsal column with a single electrode array that has a number of lateral contacts. Stimulating at the centre of the electrode and then measuring the amplitudes at each of the lateral contacts thus reveals the electrophysiological midline. The midline is identified by comparing the amplitudes of the responses at the various contacts and identifying the maximum amplitude. This requires an electrode with a large number of lateral spaced contacts and a stimulating electrode that produces a predominantly midline response.

Notably, the method of FIG. 5 does not require patient feedback so that the patient can remain under general anaesthetic throughout. Moreover, this method avoids the need for more complex recording of somatosensory cortex potentials. Further, because the patient is under general anaesthetic the possible recruitment of motor and/or pain fibres by the large stimulus delivered by probe electrode 500 will not cause patient discomfort.

FIGS. 6 to 11 illustrate the detection of lateral lead position by reference to the production of late responses, or motor activity, in accordance with another embodiment of the present invention. A patient had been previously approved for the implantation of a spinal cord stimulator to treat their pain. The patient was anaesthetised and prepared for paddle lead implantation. Once in place the lead was connected to a stimulating and recording system and ECAPs were monitored during surgery. The S4 Lamitrode electrode array 602 was inserted rostrally and was connected to channels 1 to 4 of the stimulating and recording system, while the S8 Lamitrode electrode array 604 was inserted caudally and connected to channels 9 to 16 of the stimulating and recording system, in the manner shown in FIG. 6*a*.

Figure 6A:
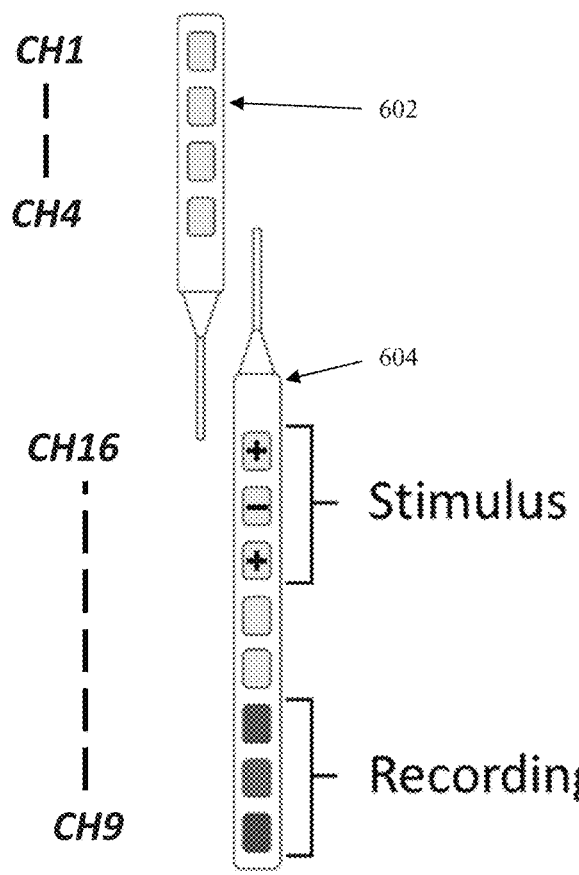
FIG. 6a illustrates electrode array positioning and channel allocations in accordance with another embodiment of the invention.
Figure 6B:
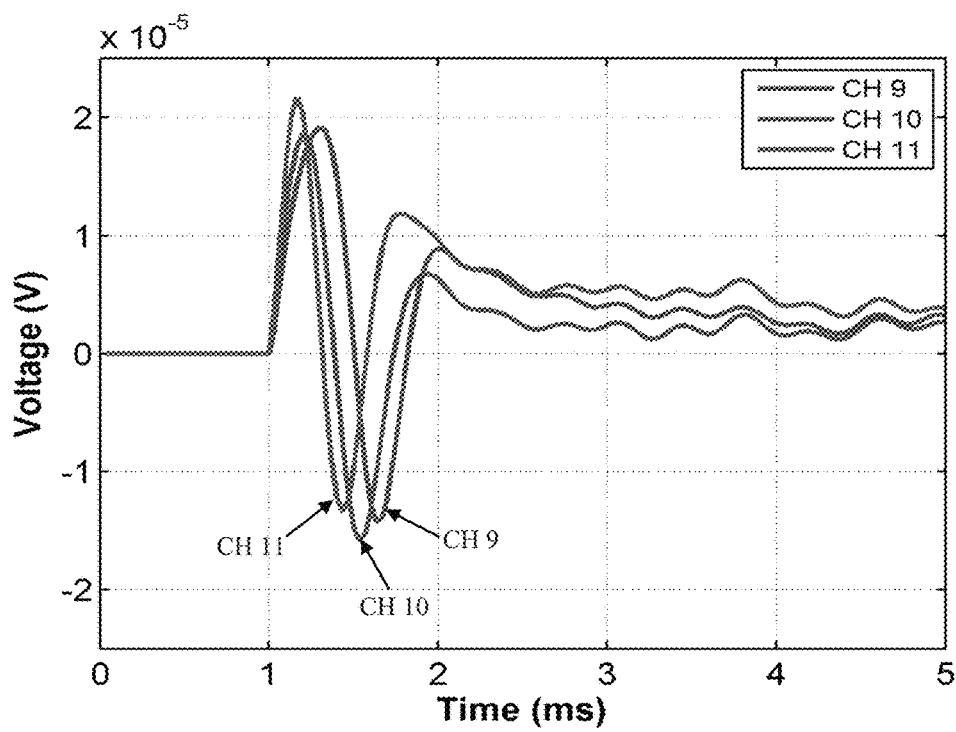

ECAPs were recorded on the S8 Lamitrode both during the procedure and while closing, with stimulation on either the S4 or S8 Lamitrode. FIG. 6*b* shows ECAP signals recorded from the caudal end (i.e. from channels 9-11) of the S8 Lamitrode 602, while stimulating at the rostral end (i.e. channels 14-16, in tripolar configuration).

Figure 7A:
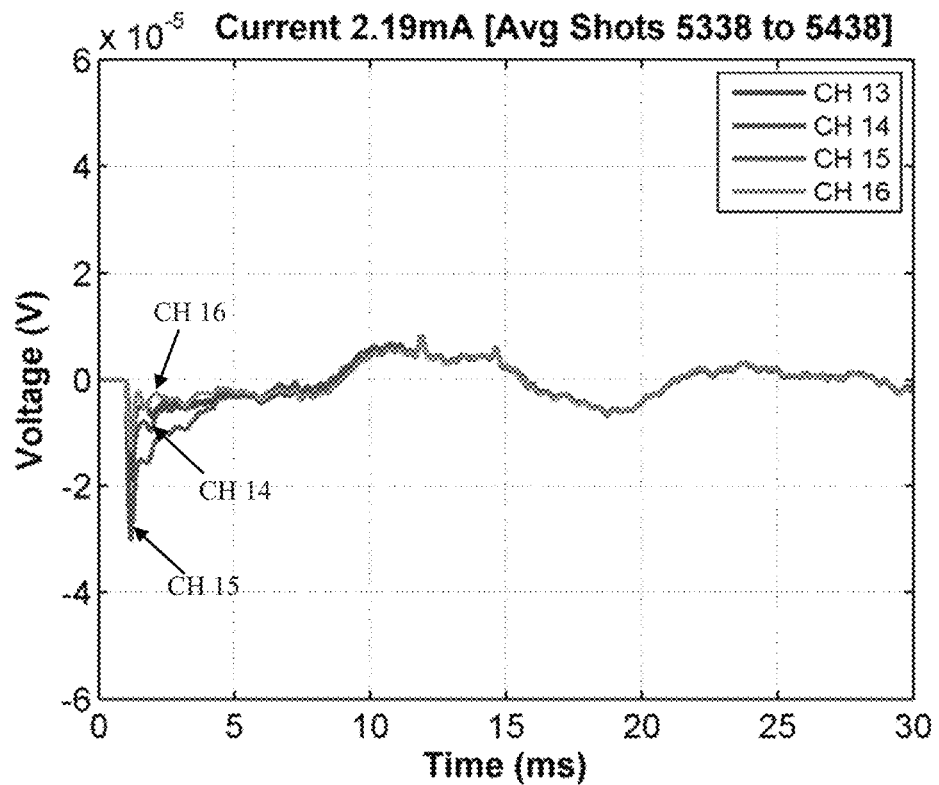
FIGS. 7a and 7b show recordings obtained from electrodes 13-16 during the implantation procedure.
Figure 7B:
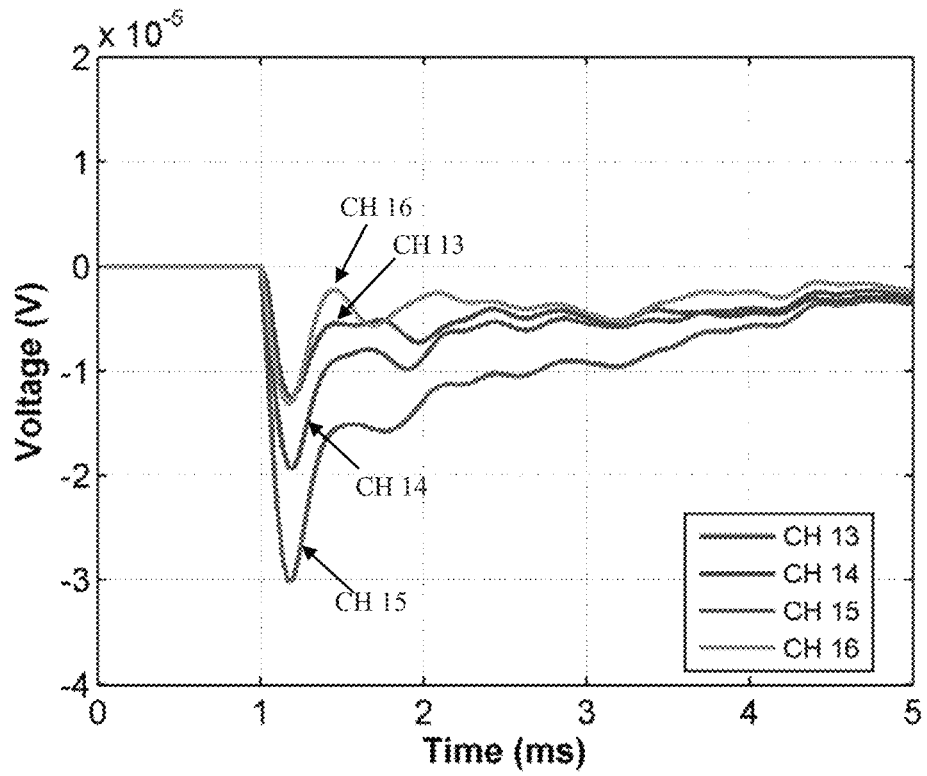

FIG. 7*a* shows recordings obtained from electrodes 13-16 during the procedure, while FIG. 7*b* is an enlarged view of the recordings of FIG. 7*a* during the time period 0-5 ms. Notably, no late responses can be seen in the time period 5-25 ms in FIG. 7*a*. In FIG. 7*b*, small ECAP signals can be seen propagating from CH16 to CH13.

Figure 8A:
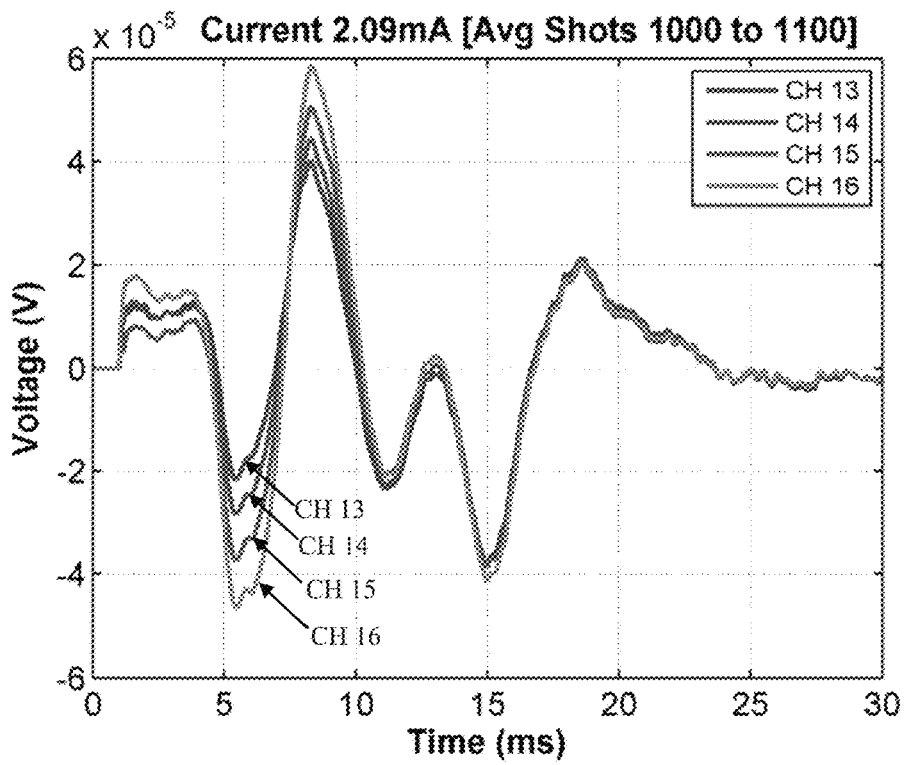
FIGS. 8a and 8b show recordings obtained from electrodes 13-16 during closing.
Figure 8B:
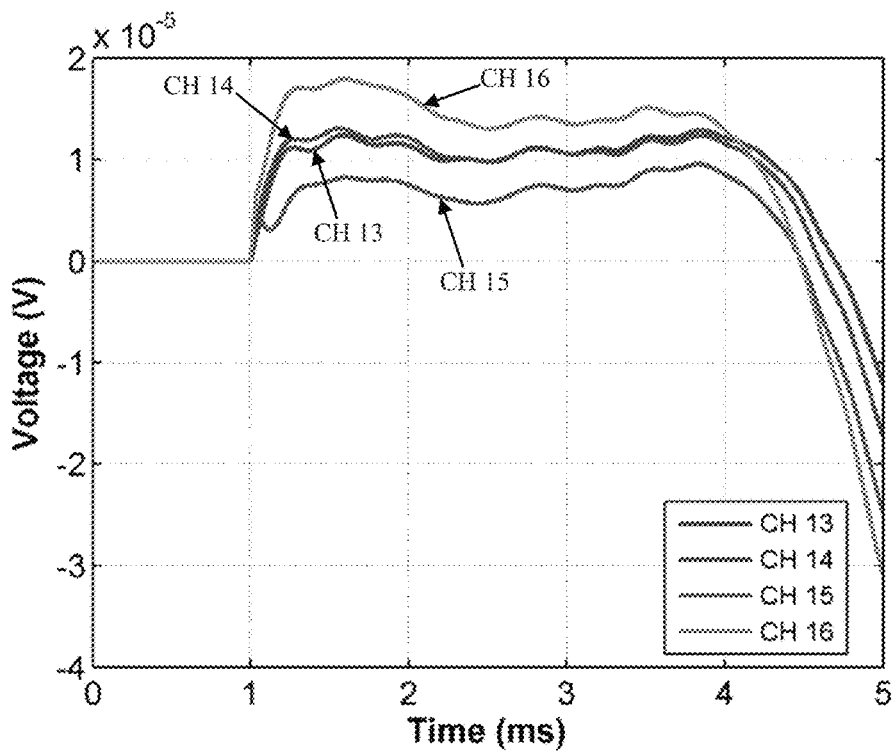

FIG. 8*a* shows recordings on electrodes 13-16 during closing, while FIG. 8*b* is an enlarged view of the recordings of FIG. 8*a* during the time period 0-5 ms. Strong late responses are visible in FIG. 8*a* in the time period 5-25 ms, which corresponded with observed patient twitching. In FIG. 8*b*, no ECAP signals can be seen propagating from Ch 16-13.

Due to the strong twitching observed in the patient during closing, the current was not increased beyond 2.2 mA, while it was previously increased beyond that level during the procedure without issue. During the procedure late responses were observed at 3.39 mA, although these were significantly smaller (<50%) than those observed during closing at 2.2 mA (less than 60% of that current).

Figure 9A:
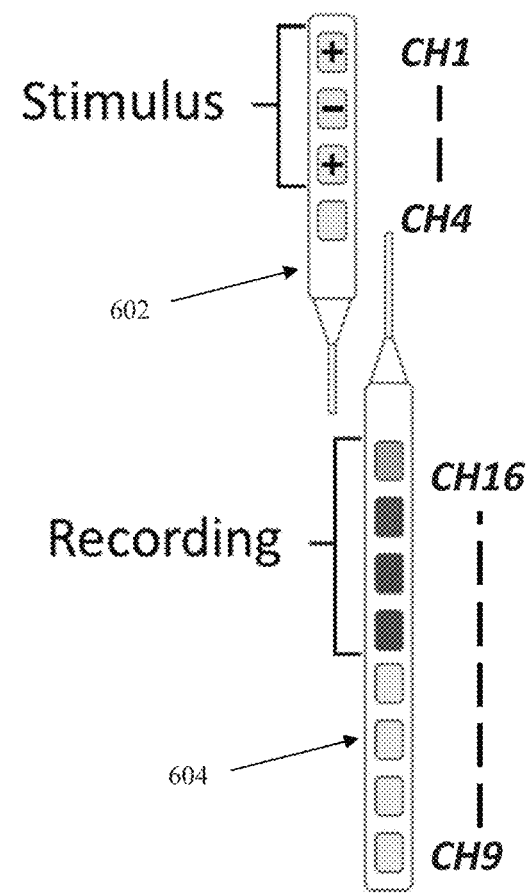
FIG. 9a illustrates electrode array positioning and channel allocations in accordance with another embodiment of the invention.

FIG. 9*a* shows the electrode configurations used to obtain the data of FIGS. 9*b*, 9*c*, 10*a* and 10*b*. In particular, stimuli were delivered by channels 1-3 on electrode array 602, while recordings were taken from channels 16-13 on electrode array 604.

Figure 9B:
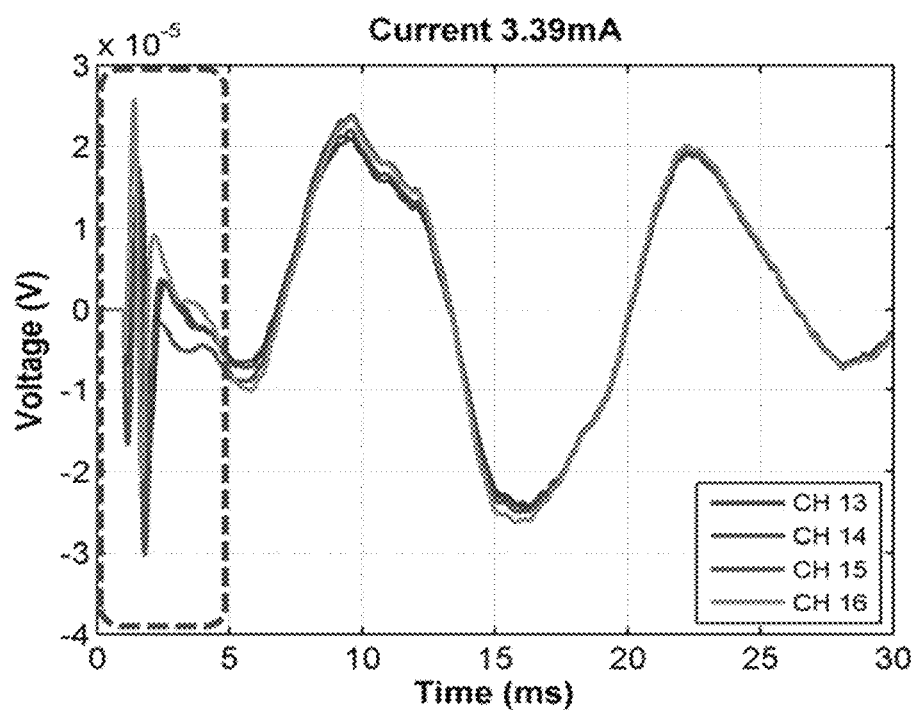
FIGS. 9b and 9c illustrate ECAP signals obtained, during the procedure, at 3.39 mA of stimulation.
Figure 9C:
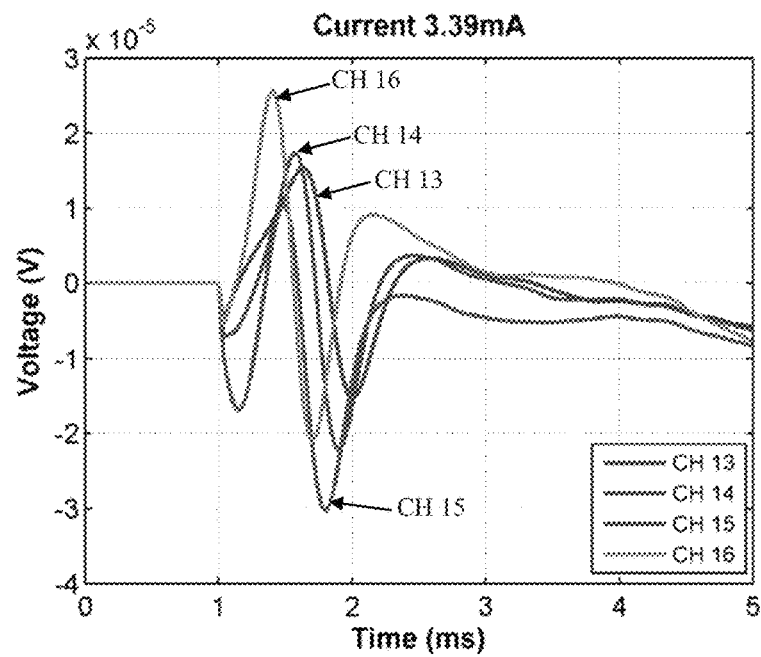

FIG. 9*b* illustrates ECAP signals propagating down the S8 lead 604, during the procedure, at 3.39 mA of stimulation. FIG. 9*c* is an enlarged view of the recordings of FIG. 9*b*, during the period 0-5 ms.

Figure 10A:
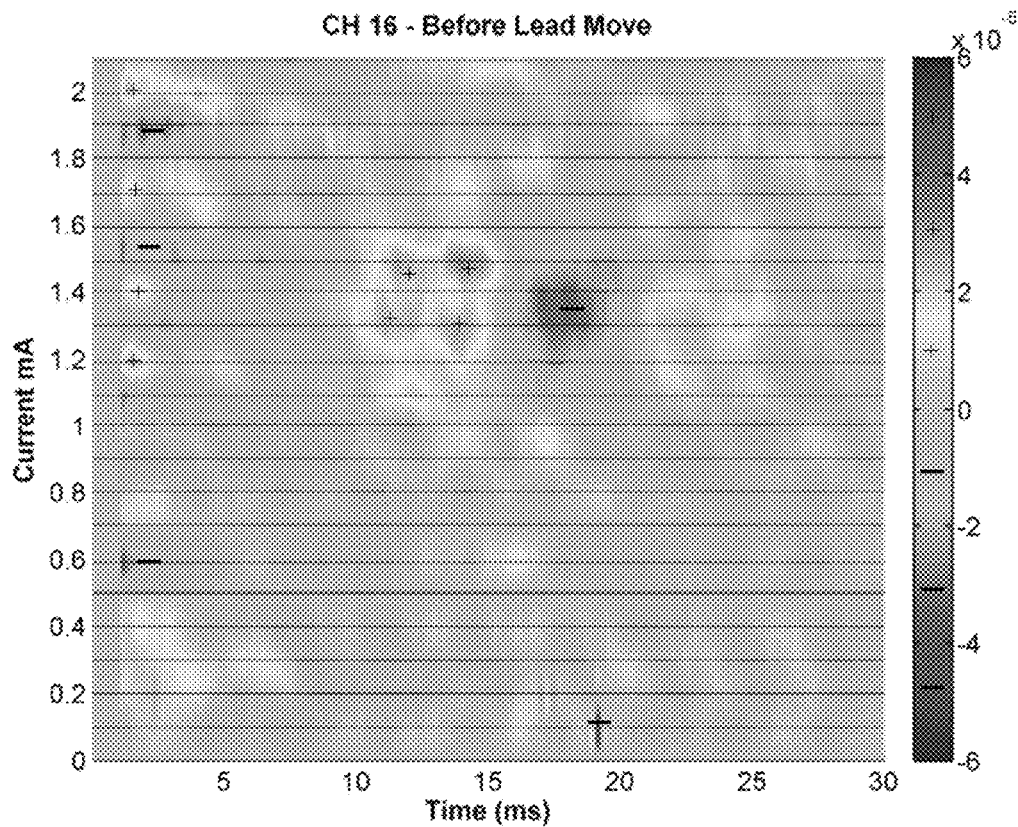
FIG. 10a is a plot of ECAP signal strength obtained on Channel 16, during the procedure, as the stimulus current was increased from zero to 2.2 mA.
Figure 10B:
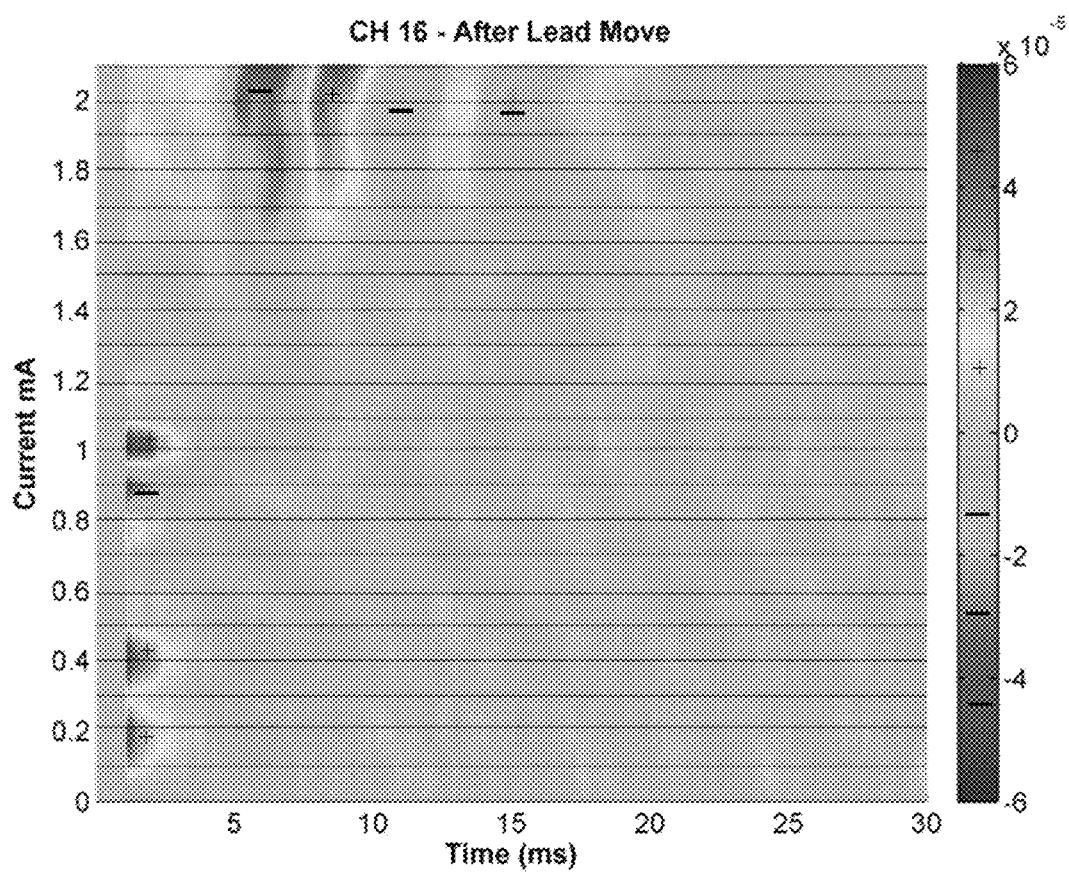
FIG. 10b is a plot of ECAP signal strength obtained on Channel 16, during closing, as the stimulus current was increased from zero to 2.2 mA.

FIG. 10*a* is a plot of signal strength obtained on Channel 16, during the procedure, as the stimulus current was increased to 2.2 mA. FIG. 10*b* is a plot of signal strength obtained on Channel 16, during closing, as the stimulus current was increased to 2.2 mA. FIG. 10*b* shows the appearance of the late response at approximately 1.7 mA during closing, between 5 and 15 ms, which continues to increase with increasing current above 1.7 mA. In contrast, no late response is observed during the procedure, i.e. in FIG. 10*a*.

Figure 11:
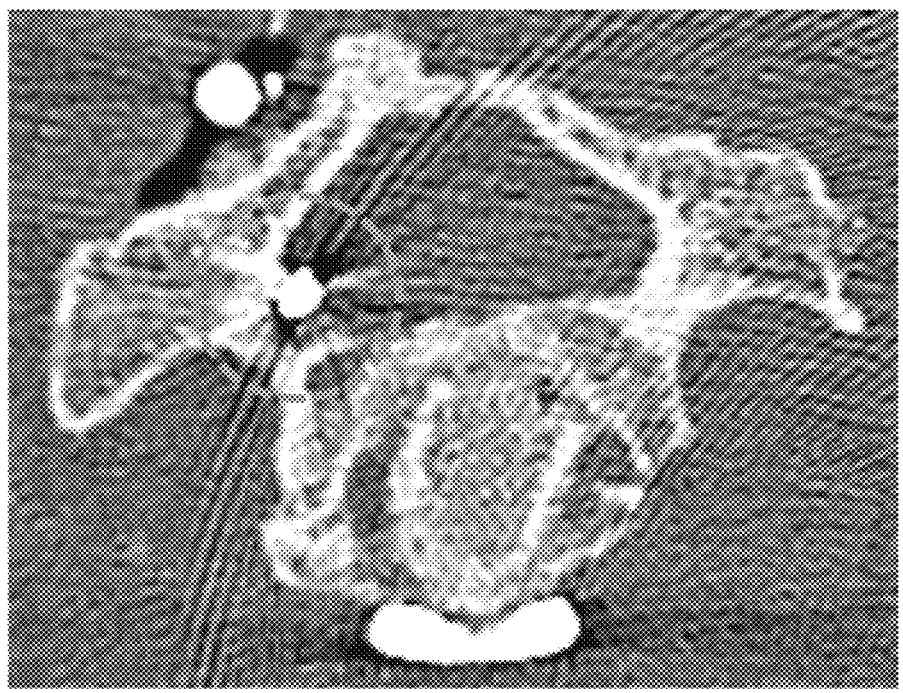
FIG. 11 is a post operative CT image illustrating the lateral location of the lead causing the late responses.

To explain the results of FIGS. 9 and 10, the electrophysiological position was correlated with an anatomical post-operative CT image, shown in FIG. 11. The CT image confirmed that the S4 lead was lateral on the left side, in particular being 15 mm left of midline at the top of C6, and being 9 mm left of midline at the bottom of C7. The proximity to the dorsal roots coincides with an early onset of the late response and lack of ECAP signals. Thus, stimulating on the S8 Lamitrode 604 showed no significant difference in ECAP amplitude for similar current amplitudes, and no sign of a late response. Stimulating on the S4 lead showed a decrease in the amplitude of the ECAP and a subsequent increase in the late response during closing. The appearance of late responses coincided with an increase in muscle activity—observed as twitching in the patient.

FIGS. 6 to 11 thus illustrate that monitoring the amplitude and latency of the ECAP as well as late response during lead insertion is a useful, accessible tool to aid lead placement. The data shows that it is possible to determine if the lead is lateral, near the dorsal roots and estimate its orientation with respect to the physiological midline of the spinal cord. Examining the presence of late responses can identify the mediolateral location of the lead. Late responses are related to the activation of roots and therefore if two leads are implanted and late responses are only seen on one side this would indicate that that lead is closer to the roots.

FIG. 12 illustrates another embodiment of the invention, in which the dorsal-ventral depth of the electrode, or its relative position from the surface of the spinal cord, is determined. In this embodiment, the probe electrode comprises two sets of stimulating contacts, each set being at a unique height above the dorsal column.

Figure 12A:
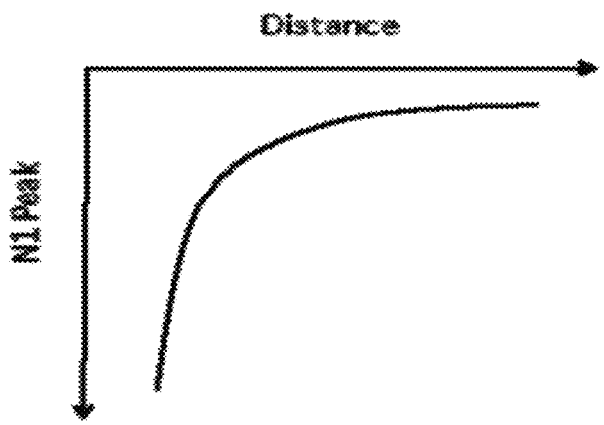
FIG. 12A illustrates variation of the amplitude of the observed ECAP response with the distance of the axon from the recording electrode.
Figure 12B:
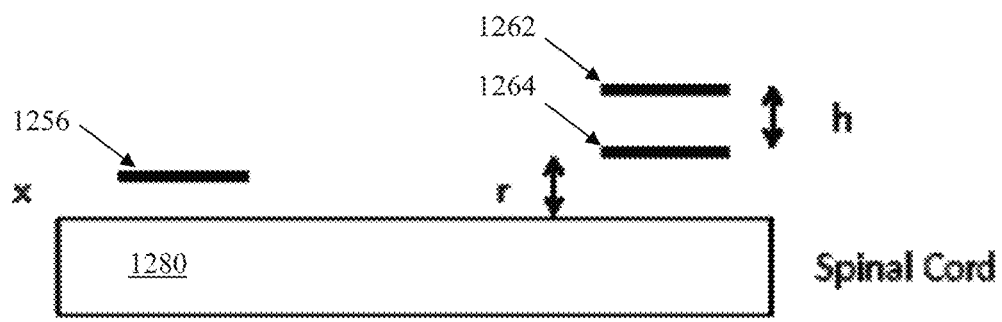
FIG. 12b illustrates an embodiment for assessing dorsoventral electrode position.

FIG. 12A illustrates how the amplitude of the observed ECAP response, as measured by the negative amplitude of the N1 peak, varies with the distance of the axon from the recording electrode. As can be seen from FIG. 12A, larger responses are observed if the fibres are closer to the electrodes, and the amplitude of the observed response varies with the distance r from the fibre by approximately $1/r^2$. The present embodiment recognises that a relative measure of the distance (x) of the electrode 1256 from the spinal cord 1280 can be obtained in the following manner. Consider a probe electrode 1260 with a least two electrode contacts 1262, 1264, which are separated by a vertical distance h above the spinal cord, as shown in FIG. 12*b*. The probe electrode height separation h can be precisely known. As discussed above in relation to FIG. 5, the electrode contacts 1262 and 1264 can each be made to extend mediolaterally from one side of the cord to other in such a manner as to recruit the maximal amount of fibres of the dorsal column of the cord 1280.

The probe electrodes 1262, 1264 are preferably mounted on a surgical tool and inserted in the retrograde manner in the epidural space opposite to the direction of the insertion of the SCS electrode 1256, in the manner shown in FIG. 5*a*. The probe electrode is stimulated in an alternate manner between the two electrode positions from the upper position 1262 to the lower position 1264. The frequency of the stimulation will allow the convenient measurement of the ECAP responses by the SCS electrode 1256 from both stimulating electrodes 1262, 1264.

Figure 12C:
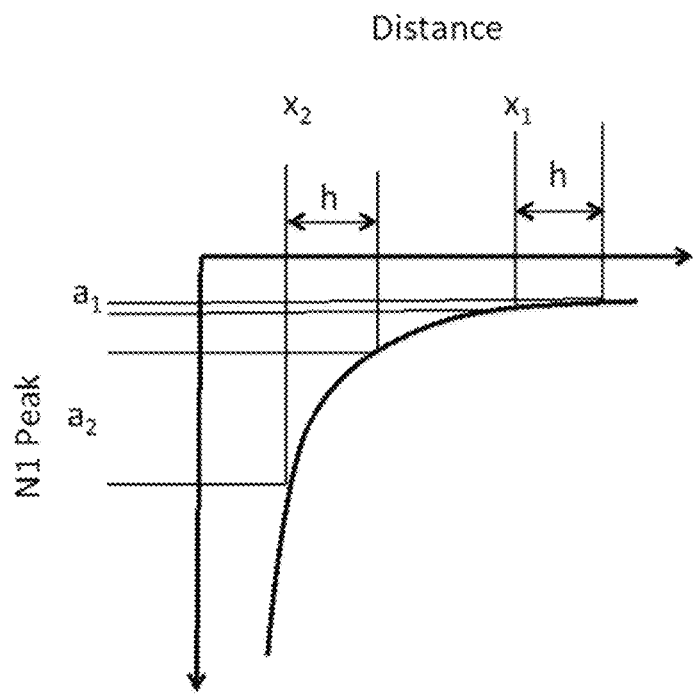
FIG. 12c illustrates observed ECAPs at differing electrode heights.

The distance x between the SCS electrode 1256 and the spinal cord 1280 can vary with insertion, or patient movement such as breathing. The height r of the stimulating electrode 1264 is unknown, but remains fixed with respect to the spinal cord 1280 due to the temporary fixing of the probe electrodes throughout the procedure. As illustrated in FIG. 12*c*, the relative distance from the cord 1280 to the SCS electrode 1256 can be determined by examining the difference in the observed ECAP amplitudes evoked by delivering the same intensity stimuli from the respective electrodes 1262, 1264.

Suitable adjustment of FIG. 12*c* may allow for the curve to be stepped to account for the transition of the propagating electric field from tissue, to the dielectric substrate material bearing electrodes 1262, 1264. Moreover, while electrode 1262 is sensing/stimulating, electrode 1264 should be electrically floating to minimise shielding of the interaction between electrode 1262 and the spinal cord 1280.

As shown in FIG. 12*c*, the amplitude difference α of the ECAP as measured by the N1 peak from the two different height probe electrodes is sensitive to the height of the electrode 1256 above the spinal cord 1280. The closer the measurement electrode 1256 is to the cord 1280, the larger the amplitude α of the differences, noting $\alpha_2 > \alpha_1$ in FIG. 12*c*.

Figure 13:
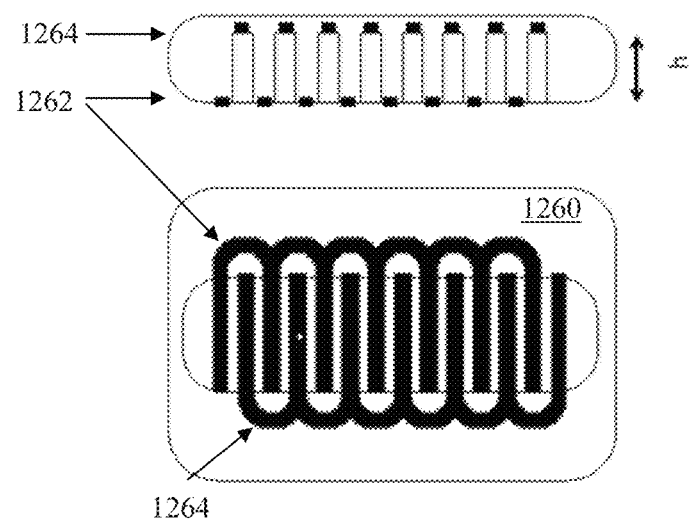
FIG. 13 illustrates a probe electrode arrangement for assessing electrode array height.

The design of the probe electrode 1260 needs to be considered carefully. It is required to stimulate the same fibres of the spinal cord 1280, from two (or more) different heights. The stimulation location in the caudal rostral direction for the two stimulating electrodes should ideally be at the same caudal-rostral location or as close to each other as possible so as the ECAP responses produced have the same distance to propagate to avoid the problem of different propagation distances resulting in different amplitudes of response. An electrode contact 1260 that achieves this arrangement is depicted in FIG. 13, in both elevation and plan view. It consists of interposed electrode contacts, whereby one set 1262 of contacts is present on the surface and the other set 1264 is separated by distance (h) at another plane in the electrode. The digits are connected together and form a single large stimulating electrode of a wide extent mediolaterally, and with two alternative heights above the dorsal column. Such embodiments thus recognise that not only is it important to be able to position the lead in the dorsolateral and rostrocaudal direction to stimulate the appropriate dermatome, it also important to know where the lead is in the dorsal ventral direction. The distance from the spinal cord to the electrode in the dorsal ventral direction affects both the power consumption and the degree to which adjustments of the stimulation current can control the location and strength of the paraesthesia or level of pain relief. For closed loop control of SCS, the closer the lead is to the spinal cord the smaller the current that is required to stimulate the target. In turn this corresponds to a larger amplitude of the actual compound action potential generated by a similar size current. Sense electrodes closer to the spinal cord will sense a stronger observed signal for a given ECAP, as compared to sense electrodes further away, improving signal to noise quality in ECAP measurements. Increasing the amplitude of the ECAP is desirable to allow finer closed loop control. Positioning electrodes closer to the dura also results in lower currents required for stimulation and lower corresponding artifacts of stimulation in ECAP measurement.

Figure 14A:
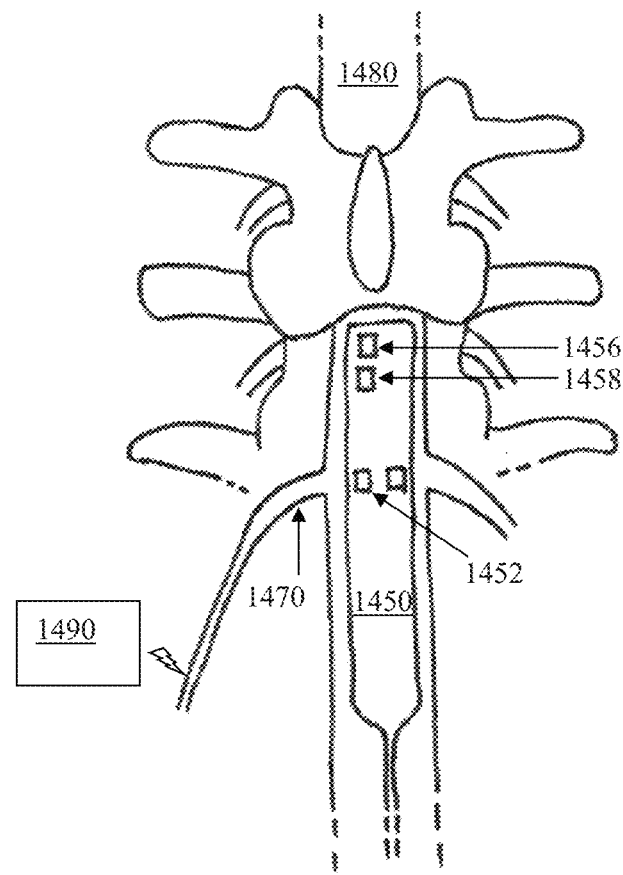
FIGS. 14a and 14b illustrate another embodiment of the invention in which ECAPs evoked directly on the spinal cord are combined with peripheral nerve stimulation.

FIG. 14a illustrates a further embodiment of the invention, in which ECAPs evoked directly on the spinal cord are combined with peripheral nerve stimulation, whereby the rostrocaudal location of the lead can be identified. In this embodiment, it is desired to position a stimulus electrode 1452 of an electrode array 1450 physiologically adjacent to a selected nerve root 1470 with an associated dermatome within which paraesthesia is required. A TENS machine 1490 is used to stimulate the peripheral nerve(s) associated with nerve root 1470, thereby evoking compound action potentials which propagate rostrally to the brain via nerve root 1470. TENS machine is operated at a fixed location and at a fixed intensity so as to produce a train of substantially constant action potentials. Simultaneously, the chosen stimulus electrode 1452 directly stimulates the spinal cord 1480. Sense electrodes 1456 and 1458 sense the resultant neural activity produced from 1490 and 1452, as it continues to propagate rostrally. The present embodiment recognises that the ECAPs evoked from stimulus electrode 1452 collide with, or interfere with, the compound action potentials evoked at the periphery by TENS device 1490, and further, that the maximal interference between the two types of ECAPs occurs when the location of electrode 1452 is optimal physiologically relative to nerve root 1470. Accordingly, the method can be performed while adjusting the caudorostral position of array 1450 to seek an array location at which maximal ECAP interference occurs. In other embodiments the sense electrode(s) may be positioned on a separate sense electrode array and for example may be temporarily implanted only for the duration of the implantation procedure.

Figure 14B:
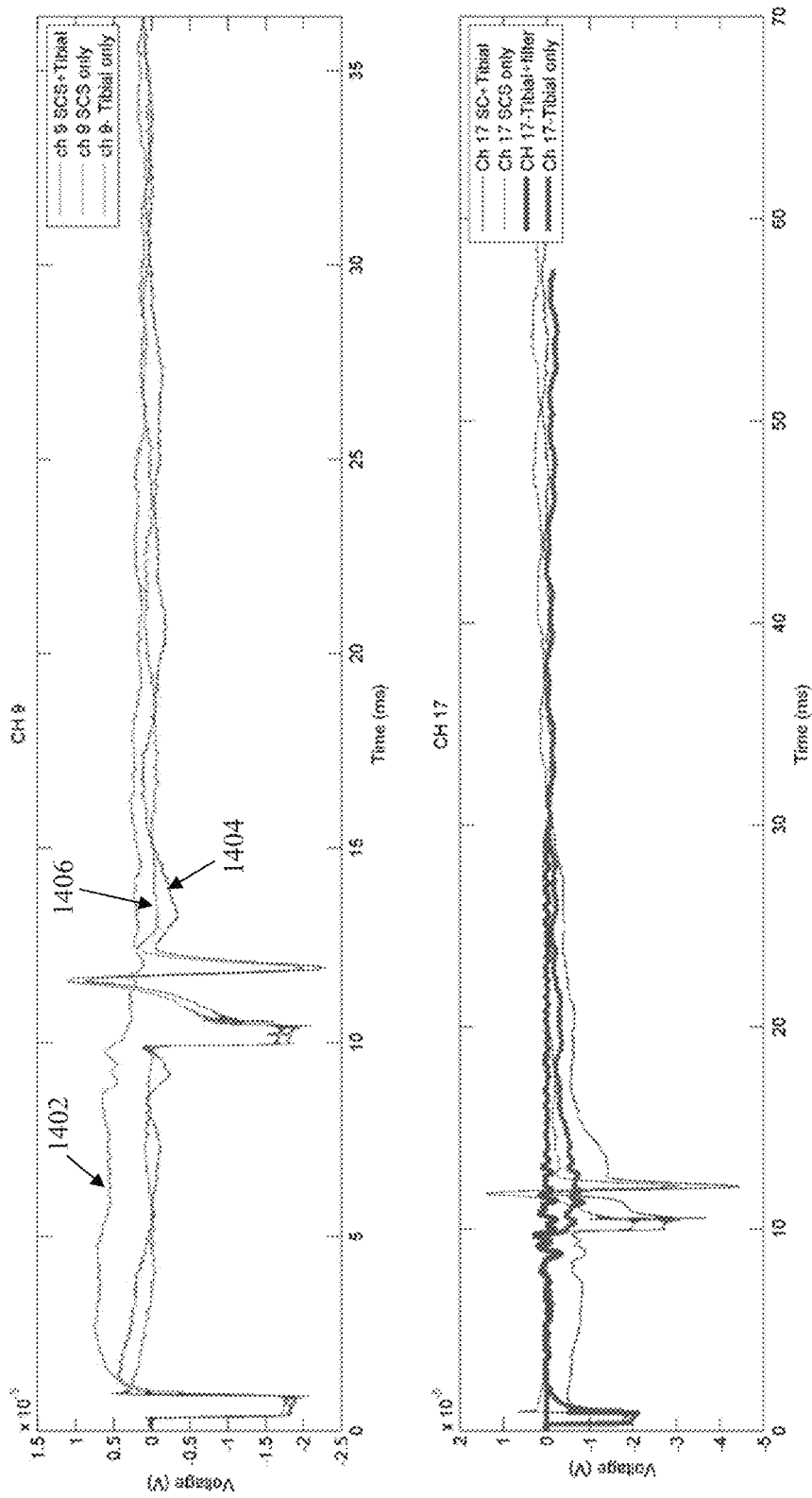

FIG. 14b illustrates such ECAP interference or collision. FIG. 14b shows the observed response 1402 from a single electrode in response to tibial nerve stimulation alone, the response 1404 from tibial nerve stimulation simultaneously with spinal cord stimulation, and the response 1406 observed when performing spinal cord stimulation only, without peripheral stimulation. The delay time to the dorsal column stimuli which produces the most attenuation allows estimation of the total length of the fibre from the point where the stimulus is presented.

The ability to monitor, and control optimisation of, the mediolateral, caudorostral and/or dorsoventral location of the electrode, relative to physiological characteristics of the dorsal columns rather than anatomical markers, will thus enable a much higher precision of implantation. The present invention may thus provide feedback to a surgeon that allows the lead to be steered to optimize the final implanted location of the spinal cord stimulation lead. To do so requires surgical tools to assist in the steering and placement of electrodes. Some embodiments may therefore involve a lead comprising a longitudinal pocket or similar parts designed to receive an insertion tool.

In all described embodiments the determined position information can be presented to the surgeon by any suitable means, such as by an acoustic tone with pitch indicating relative height or position, or a visual indicia, or otherwise.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. A method of estimating a position of an electrode array relative to a nerve, the electrode array being implanted adjacent to the nerve, wherein the electrodes of the electrode array are configured to apply stimulation or sense evoked compound action potentials (ECAPs), the method comprising:
    applying stimulation at at least one electrode;
    measuring at least one of an amplitude and latency of the ECAPs;
    increasing a stimulation intensity, and repeating the applying and the measuring, until an onset of a late response is observed;
    measuring at least one of an amplitude and latency of the late response; and
    estimating a position of the electrode array relative to the nerve based on the amplitude and latency of at least one of the ECAPs and the late response.

2. The method of claim 1, further comprising:
    monitoring for an occurrence of muscle twitching, and
    correlating the onset of the late response with the occurrence of muscle twitching, wherein the correlation is used to estimate the position of the electrode array.

3. The method of claim 1, wherein estimating the position of the electrode array comprises using the onset of the late response to indicate that the electrode array is proximal to dorsal roots.

4. The method of claim 1, wherein estimating the position of the electrode array comprises using a lack or decreased amplitude of the ECAPs to indicate that the electrode array is proximal to dorsal roots.

5. The method of claim 1, further comprising estimating a position of the electrode array based on a collision of the ECAPs with peripherally evoked compound action potentials.

6. The method of claim 5, further comprising causing a collision of the ECAPs with the peripherally evoked compound action potentials by introducing a delay between consecutive stimuli.

7. The method of claim 1, wherein the electrode array is a paddle lead.

8. The method of claim 1, wherein the electrode array is a percutaneous lead.

9. A system for estimating a position of an electrode array relative to a nerve, the system comprising:
    an electrode array configured to be implanted adjacent to the nerve, and comprising at least one electrode configured to apply stimulation or sense compound action potentials (ECAPs); and
    a controller configured to:
        apply stimulation at at least one electrode;
        measure at least one of an amplitude and latency of ECAPs;
        increase a stimulation intensity and repeat the applying and the measuring until an onset of a late response is observed;
        measure at least one of an amplitude and latency of the late response; and estimate a position of the electrode array relative to the nerve based on the amplitude and latency of at least one of the ECAPs and the late response.

10. The system of claim 9, wherein the controller is further configured to monitor for an occurrence of muscle twitching, to correlate the onset of the late response with the occurrence of muscle twitching, and to use the correlation to estimate the position of the electrode array.

11. The system of claim 9, wherein the controller is configured to use the onset of the late response to indicate that the electrode array is proximal to dorsal roots.

12. The system of claim 9, wherein the controller is configured to indicate that the electrode array is proximal to dorsal roots based on a lack or decreased amplitude of the ECAPs.

13. The system of claim 9, wherein the controller is configured to estimate a position for implanting the electrode array based on a collision of the ECAPs with peripherally evoked compound action potentials.

14. The system of claim 13, wherein the controller is configured to cause a collision of the ECAPs with the peripherally evoked compound action potentials by introducing a delay between consecutive stimuli.

15. The system of claim 9, wherein the electrode array is a paddle lead.

16. The system of claim 9, wherein the electrode array is a percutaneous lead.

* * * * *